US009100592B2

(12) United States Patent
Chapman

(10) Patent No.: US 9,100,592 B2
(45) Date of Patent: Aug. 4, 2015

(54) SYSTEM AND METHOD FOR PRODUCING COLOR SHIFTING OR GLOSS EFFECT AND RECORDING MEDIUM WITH COLOR SHIFTING OR GLOSS EFFECT

(71) Applicant: Xerox Corporation, Norwalk, CT (US)

(72) Inventor: Edward N. Chapman, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 43 days.

(21) Appl. No.: 14/030,038

(22) Filed: Sep. 18, 2013

(65) Prior Publication Data
US 2015/0077804 A1    Mar. 19, 2015

(51) Int. Cl.
H04N 1/40 (2006.01)
H04N 1/32 (2006.01)
H04N 1/60 (2006.01)
C12N 15/10 (2006.01)

(52) U.S. Cl.
CPC ........ *H04N 1/32309* (2013.01); *C12N 15/1048* (2013.01); *H04N 1/3232* (2013.01); *H04N 1/32352* (2013.01); *H04N 1/40* (2013.01); *H04N 1/60* (2013.01); *H04N 2201/0094* (2013.01); *H04N 2201/327* (2013.01); *H04N 2201/3233* (2013.01); *H04N 2201/3271* (2013.01); *H04N 2209/00* (2013.01)

(58) Field of Classification Search
USPC .................................. 358/1.9, 2.1, 3.28, 3.31
See application file for complete search history.

(56) References Cited

U.S. PATENT DOCUMENTS

| 5,286,286 A | 2/1994 | Winnik et al. |
| 5,734,752 A | 3/1998 | Knox |
| 7,324,241 B2 | 1/2008 | Eschbach et al. |
| 7,391,529 B2 | 6/2008 | Glaspy, Jr. et al. |

(Continued)

FOREIGN PATENT DOCUMENTS

| CA | 2788413 A1 | 8/2011 |
| EP | 2528746 B1 | 8/2011 |
| WO | WO 2011/091969 A1 | 8/2011 |

OTHER PUBLICATIONS

"Detecting Counterfeit Money, Part II: Color-Shifting Numbers", Fraud Fighter, Fraud Prevention Blog, http://central.fraudfighter.com/counterfeit-detection-id-verification/bid/42471/Detecting-Counterfeit-Money-Part-II-Color-shifting-Numbers, posted by Gary Satanovsky; Jun. 27, 2010.

(Continued)

*Primary Examiner* — Jamares Q Washington
(74) *Attorney, Agent, or Firm* — Basch & Nickerson LLP

(57) ABSTRACT

A gloss effect image pattern is created on a recording medium by electronically creating a first electronic pattern ink, the first electronic pattern ink including a first color and including holes, the holes representing areas in the first electronic pattern ink wherein the first color is absent; electronically creating a second electronic pattern ink using the first color and including filled holes, the filled holes of the second electronic pattern ink representing areas in the second electronic pattern ink filled with a second color, the second color being different than the first color; electronically creating an electronic image region; electronically painting, using the first electronic pattern ink, a background of the electronic image region; electronically painting, using the second electronic pattern ink, a foreground of the electronic image region; and rendering, using marking materials, the electronic image region on the recording medium.

12 Claims, 17 Drawing Sheets

(56) References Cited

U.S. PATENT DOCUMENTS

| | | | |
|---|---|---|---|
| 7,639,400 B2 | 12/2009 | Hains | |
| 7,852,515 B2 | 12/2010 | Eschbach et al. | |
| 8,064,100 B2 | 11/2011 | Braun et al. | |
| 8,111,432 B2 | 2/2012 | Eschbach et al. | |
| 8,147,932 B2 | 4/2012 | Despland et al. | |
| 8,310,718 B2 | 11/2012 | Chapman et al. | |
| 8,894,098 B2 | 11/2014 | MacPherson et al. | |
| 2002/0160194 A1 | 10/2002 | Phillips et al. | |
| 2003/0170471 A1 | 9/2003 | Seto et al. | |
| 2003/0184613 A1 | 10/2003 | Nakamura et al. | |
| 2007/0017990 A1 | 1/2007 | Katsurabayashi | |
| 2007/0139680 A1 | 6/2007 | Eschbach et al. | |
| 2007/0139681 A1 | 6/2007 | Eschbach et al. | |
| 2007/0200002 A1* | 8/2007 | Raksha et al. | 235/491 |
| 2007/0262579 A1 | 11/2007 | Bala et al. | |
| 2007/0281140 A1 | 12/2007 | Haubrich et al. | |
| 2008/0080000 A1* | 4/2008 | Kadota | 358/1.15 |
| 2008/0122217 A1 | 5/2008 | Rancien et al. | |
| 2008/0134920 A1* | 6/2008 | Foresti et al. | 101/491 |
| 2008/0299333 A1 | 12/2008 | Bala et al. | |
| 2008/0302263 A1 | 12/2008 | Eschbach et al. | |
| 2009/0072185 A1 | 3/2009 | Raksha et al. | |
| 2009/0207433 A1 | 8/2009 | Wang et al. | |
| 2009/0262400 A1 | 10/2009 | Eschbach et al. | |
| 2010/0128321 A1 | 5/2010 | Wang et al. | |
| 2010/0214595 A1 | 8/2010 | Chapman et al. | |
| 2010/0238513 A1 | 9/2010 | Morales et al. | |
| 2011/0127331 A1 | 6/2011 | Zhao et al. | |
| 2011/0191670 A1 | 8/2011 | Hoppenot et al. | |
| 2011/0205569 A1 | 8/2011 | Eschbach et al. | |
| 2012/0140290 A1 | 6/2012 | Eschbach et al. | |
| 2013/0113200 A1 | 5/2013 | Lister | |
| 2013/0128319 A1 | 5/2013 | Kenehan | |
| 2013/0161939 A1 | 6/2013 | Kasperchik et al. | |
| 2014/0085392 A1 | 3/2014 | Chapman et al. | |

OTHER PUBLICATIONS

Co-Pending U.S. Appl. No. 14/270,868, filed May 6, 2014.
Co-Pending U.S. Appl. No. 14/030,020.
Co-Pending U.S. Appl. No. 14/030,025.
Co-Pending U.S. Appl. No. 14/030,032.
Co-Pending U.S. Appl. No. 14/030,046.
Co-Pending U.S. Appl. No. 14/030,054.
Co-Pending U.S. Appl. No. 14/030,062.
Office Action Issued Jan. 30, 2015 for Co-Pending U.S. Appl. No. 14/030,025.
Office Action Issued Feb. 23, 2015 for Co-Pending U.S. Appl. No. 14/030,032.
Office Action Issued Jan. 30, 2015 for Co-Pending U.S. Appl. No. 14/030,046.
Office Action Issued Feb. 13, 2015 for Co-Pending U.S. Appl. No. 14/030,054.
Office Action Issued Feb. 13, 2015 for Co-Pending U.S. Appl. No. 14/030,062.

* cited by examiner

SYSTEM AND METHOD FOR PRODUCING COLOR SHIFTING OR GLOSS EFFECT AND RECORDING MEDIUM WITH COLOR SHIFTING OR GLOSS EFFECT

BACKGROUND

In conventional printing processes, requiring security measures, a pattern color space having specialty imaging characteristics have been utilized to provide the security measures and prevent counterfeiting of printed materials.

In addition, in conventional printing processes, a pattern color space has been utilized, in part on variable data, such as printing logos, serial numbers, seat locations, or other types of unique identifying information on printed materials.

In security applications, it is desirable to add information to a document that prevents or hinders alterations and counterfeiting. These security elements may conflict with the overall aesthetics of the document.

Specialty imaging has been used, conventionally, in printed materials to provide fraud protection and anti-counterfeiting measures. Some examples are in prescriptions, contracts, documents, coupons, and tickets. Typically, several specialty imaging techniques are used at various positions in a document. However, specialty imaging text techniques take up space in the document.

One example of a conventional specialty imaging technique restricts designers to use rectangular areas for security elements of documents. This may be acceptable for locating security elements in headers, footers, or similar areas of documents. However, rectangular security elements may not be as "pleasing" in other document areas.

With reference to FIGS. 1 and 2, typical specialty imaging techniques are implemented in document security elements that are restricted to rectangular areas. This is an example of current specialty imaging capabilities which provide static (i.e., non-dynamic) specialty imaging marks with respect to "design" freedom.

In FIG. 1, the rectangular footer provides a logo which incorporates a GlossMark™ text in the right of the rectangular area. Also, microtext lines, another type of a rectangular element, are included as part of the table delineation in FIG. 1.

In FIG. 2, GlossMark™ text is used in the rectangular area at the bottom, a Fluorescent text is used in the rectangular area in the top left, and a microtext line is in the center left portion of a parking permit. These elements are useful in the context of security, but lack aesthetic value.

Examples of conventional specialty imaging techniques are disclosed in U.S. Pat. No. 8,310,718; U.S. Pat. No. 7,324, 241; U.S. Pat. No. 7,391,529; Published US Patent Application Number 2007/0139680; Published US Patent Application Number 2007/0139681; Published US Patent Application Number 2009/0207433; Published US Patent Application Number 2009/0262400; Published US Patent Application Number 2010/0214595; Published US Patent Application Number 2010/0238513; Published US Patent Application Number 2011/00127331; Published US Patent Application Number 2011/0191670; Published US Patent Application Number 2011/0205569; Published US Patent Application Number 2012/0140290; co-pending U.S. patent application Ser. No. 13/671,071, filed on Nov. 7, 2012; and co-pending U.S. patent application Ser. No. 13/776,868, filed on Feb. 26, 2013.

The entire content of U.S. Pat. No. 8,310,718 is hereby incorporated by reference. The entire content of U.S. Pat. No. 7,324,241 is hereby incorporated by reference. The entire content of U.S. Pat. No. 7,391,529 is hereby incorporated by reference. The entire content of Published US Patent Application Number 2007/0139680 is hereby incorporated by reference. The entire content of Published US Patent Application Number 2007/0139681 is hereby incorporated by reference. The entire content of Published US Patent Application Number 2009/0207433 is hereby incorporated by reference. The entire content of Published US Patent Application Number 2009/0262400 is hereby incorporated by reference.

The entire content of Published US Patent Application Number 2010/0214595 is hereby incorporated by reference. The entire content of Published US Patent Application Number 2010/0238513 is hereby incorporated by reference. The entire content of Published US Patent Application Number 2011/00127331 is hereby incorporated by reference. The entire content of Published US Patent Application Number 2011/0191670 is hereby incorporated by reference. The entire content of Published US Patent Application Number 2011/0205569 is hereby incorporated by reference. The entire content of Published US Patent Application Number 2012/0140290 is hereby incorporated by reference.

The entire content of co-pending U.S. patent application Ser. No. 13/671,071, filed on Nov. 7, 2012, is hereby incorporated by reference. The entire content of co-pending U.S. patent application Ser. No. 13/776,868, filed on Feb. 26, 2013, is hereby incorporated by reference.

In one conventional specialty imaging technique, the method includes defining a variable portion of the pattern color space in a page description language; defining a fixed portion of the pattern color space in the page description language; defining a bounding shape for the pattern color space in the page description language; and defining a procedure for painting the variable and fixed portions within the bounding shape in the page description language.

In this conventional specialty imaging technique, the variable portion of the pattern color space is based at least in part on variable data associated with the print job and at least one object within the print job identifies the pattern color space for a color parameter.

In another conventional security printing technique, the method includes the use of color shifting ink, which appears as one color from a certain angle and another color from another angle. In other words a special ink is required to realize the color shift effect.

For example, a printed security feature for printed currency utilizes color-shifting ink to print the numerals located in the corners on the front of the bill. More specifically, on a US $100 banknote, the green color use to print the denomination in the corners on the front of the bill will "shift" to grey and back to green as the bill is tilted back and forth to change the viewing angle.

The "optically variable ink" is not widely commercially available and cannot be replicated by any copiers, which only "see" and replicate patterns from a fixed angle.

Therefore, it is desirable to provide a specialty imaging technique, utilizing color-shifting, which does not require special inks or marking materials, and still cannot be readily replicated by conventional copiers and/or scanner.

In addition, it is desirable to provide a specialty imaging technique that is applicable to Variable-Data Intelligent PostScript™ Printware workflows and that transmit an image a single time and subsequently only submit the variable text string to the digital front end.

BRIEF DESCRIPTION OF THE DRAWING

The drawings are only for purposes of illustrating various embodiments and are not to be construed as limiting, wherein:

FIG. 21 shows a portion of a printed image having a hole to allow substrate show through.

DETAILED DESCRIPTION

Figure 1:
FIG. 1 shows an example of printed material with security elements.
Figure 2:
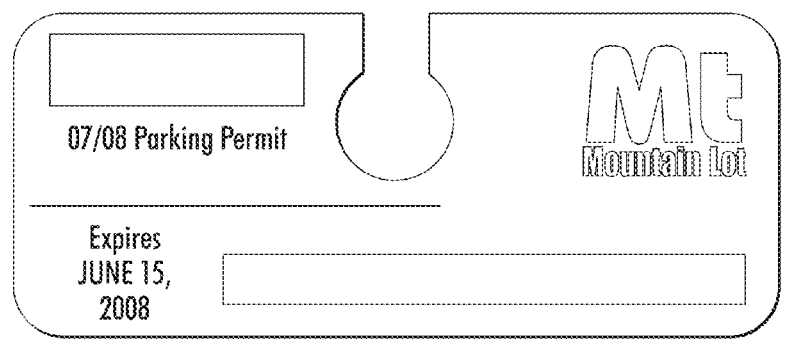
FIG. 2 shows another example of printed material with security elements.

For a general understanding, reference is made to the drawings. In the drawings, like references have been used throughout to designate identical or equivalent elements. It is also noted that the drawings may not have been drawn to scale and that certain regions may have been purposely drawn disproportionately so that the features and concepts may be properly illustrated.

The term "data" refers herein to physical signals that indicate or include information. An "image," as a pattern of physical light or a collection of data representing said physical light, may include characters, words, and text as well as other features such as graphics.

A "digital image" is by extension an image represented by a collection of digital data. An image may be divided into "segments," each of which is itself an image. A segment of an image may be of any size up to and including the whole image.

The term "image object" or "object" as used herein is believed to be considered in the art generally equivalent to the term "segment" and will be employed herein interchangeably.

In a digital image composed of data representing physical light, each element of data may be called a "pixel," which is common usage in the art and refers to a picture element. Each pixel has a location and value. Each pixel value is a bit in a "binary form" of an image, a gray scale value in a "gray scale form" of an image, or a set of color space coordinates in a "color coordinate form" of an image, the binary form, gray scale form, and color coordinate form each being a two-dimensional array defining an image.

An operation performs "image processing" when it operates on an item of data that relates to part of an image.

"Contrast" is used to denote the visual difference between items, data points, and the like. It can be measured as a color difference or as a luminance difference or both.

A digital color printing system is an apparatus arrangement suited to accepting image data and rendering that image data upon a substrate.

The "RGB color model" is an additive color model in which red, green, and blue light are added together in various ways to reproduce a broad array of colors. The name of the model comes from the initials of the three additive primary colors, red, green, and blue. The main purpose of the RGB color model is for the sensing, representation, and display of images in electronic systems. RGB is a device-dependent color model: different devices detect or reproduce a given RGB value differently, since the color elements and their response to the individual R, G, and B levels vary from manufacturer to manufacturer, or even in the same device over time. Thus, an RGB value does not define the same color across devices without some kind of color management.

The "CMYK color model" is a subtractive color model, used in color printing, and is also used to describe the printing process itself. CMYK refers to the four inks used in some color printing: cyan, magenta, yellow, and black.

"Colorant" refers to one of the fundamental subtractive C, M, Y, K, primaries, which may be realized in formulation as, liquid ink, solid ink, dye, or electrostatographic toner. A "colorant mixture" is a particular combination of C, M, Y, K colorants.

An "infrared mark" is a watermark embedded in the image that has the property of being relatively indecipherable under normal light, and yet decipherable under infrared illumination by appropriate infrared sensing devices, such as infrared cameras.

"Metameric" rendering/printing is the ability to use multiple colorant combinations to render a single visual color, as can be achieved when printing with more than three colorants.

Figure 3:
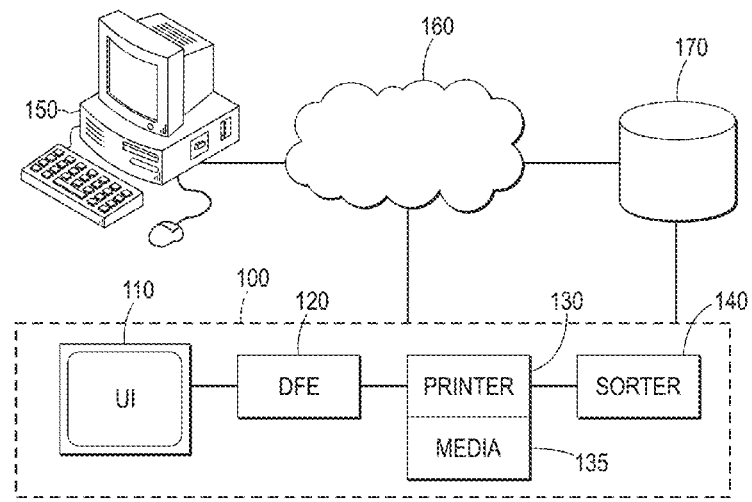
FIG. 3 is block diagram of a printing system suitable for implementing one or more aspects of the exemplary methods described herein.

With reference to FIG. 3, a printing system (or image rendering system) 100 suitable for implementing various aspects of the exemplary embodiments described herein is illustrated.

The word "printer" and the term "printing system" as used herein encompass any apparatus and/or system; such as a digital copier, xerographic and reprographic printing systems, bookmaking machine, facsimile machine, multi-function machine, ink-jet machine, continuous feed, sheet-fed printing device, etc.; which may contain a print controller and a print engine and which may perform a print outputting function for any purpose.

The printing system 100 generally includes a user interface 110, a digital front end controller 120, and at least one print engine 130. The print engine 130 has access to print media 135 of various sizes and cost for a print job.

A "print job" or "document" is normally a set of related sheets, usually one or more collated copy sets copied from a set of original print job sheets or electronic document page images, from a particular user, or otherwise related. For submission of a regular print job (or customer job), digital data is generally sent to the printing system 100.

A sorter 140 operates after a job is printed by the print engine 130 to manage arrangement of the hard copy output, including cutting functions. A user can access and operate the printing system 100 using the user interface 110 or via a workstation 150. The workstation 150 communicates with the printing system 100 via a communications network 160.

A user profile, a work product for printing, a media library, and various print job parameters can be stored in a database or memory 170 accessible by the workstation 150 or the printing system 100 via the network 160, or such data can be directly accessed via the printing system 100. One or more color sensors (not shown) may be embedded in the printer paper path, as known in the art.

Figure 4:
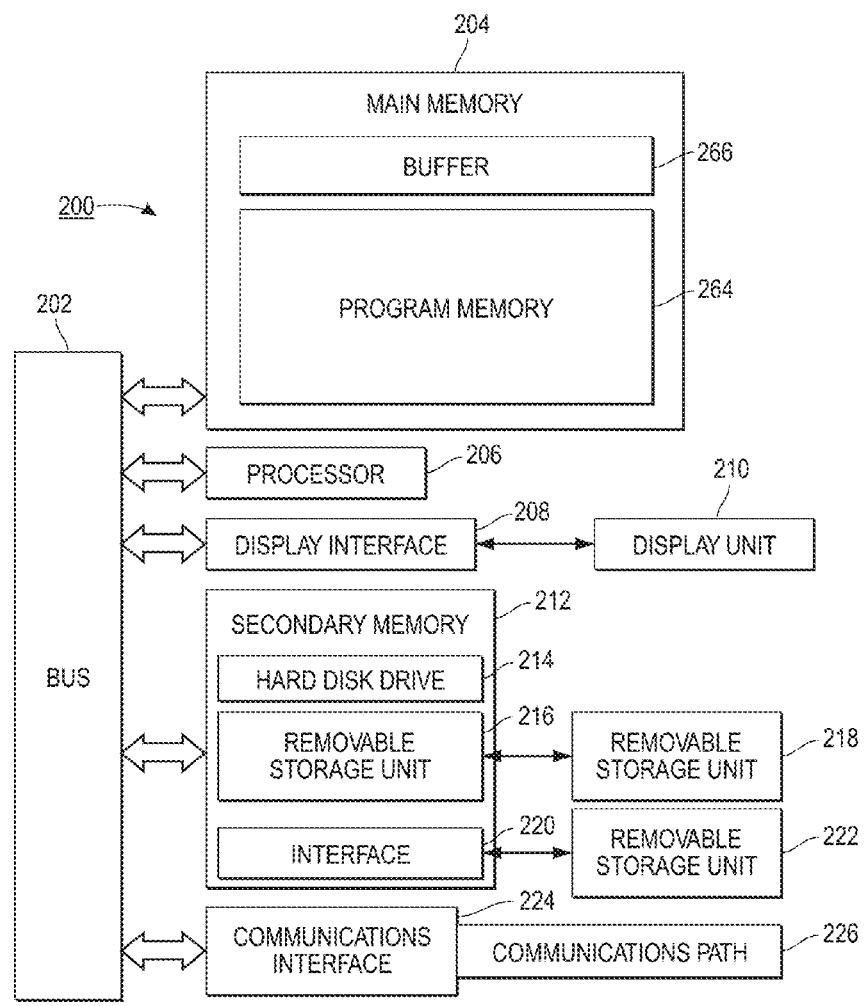
FIG. 4 is a block diagram of a digital front end controller useful for implementing one or more aspects of the exemplary methods described herein.

With respect to FIG. 4, an exemplary digital front end controller 200 is shown in greater detail. The digital front end 200 includes one or more processors, such as processor 206 capable of executing machine executable program instructions.

In the embodiment shown, the processor is in communication with a bus 202 (e.g., a backplane interface bus, cross-over bar, or data network). The digital front end 200 also includes a main memory 204 that is used to store machine readable instructions. The main memory also being capable of storing data. Main memory may alternatively include random access memory (RAM) to support reprogramming and flexible data storage. Buffer 266 is used to temporarily store data for access by the processor. Program memory 264 includes, for example, executable programs that implement the embodiments of the methods described herein. The program memory 264 stores at least a subset of the data contained in the buffer.

The digital front end 200 includes a display interface 208 that forwards data from communication bus 202 (or from a frame buffer not shown) to a display 210. The digital front end 200 also includes a secondary memory 212 includes, for example, a hard disk drive 214 and/or a removable storage drive 216, which reads and writes to removable storage 218, such as a floppy disk, magnetic tape, optical disk, etc., that stores computer software and/or data.

The secondary memory 212 alternatively includes other similar mechanisms for allowing computer programs or other instructions to be loaded into the computer system. Such mechanisms include, for example, a removable storage unit 222 adapted to exchange data through interface 220. Examples of such mechanisms include a program cartridge and cartridge interface (such as that found in video game devices), a removable memory chip (such as an EPROM, or PROM) and associated socket, and other removable units and interfaces which allow software and data to be transferred.

The digital front end 200 includes a communications interface 224, which acts as both an input and an output to allow software and data to be transferred between the digital front end 200 and external devices. Examples of a communications interface include a modem, a network interface (such as an Ethernet card), a communications port, a PCMCIA slot and card, etc.

Computer programs (also called computer control logic) may be stored in main memory 204 and/or secondary memory 212. Computer programs may also be received via a communications interface 224. Such computer programs, when executed, enable the computer system to perform the features and capabilities provided herein. Software and data transferred via the communications interface can be in the form of signals which may be, for example, electronic, electromagnetic, optical, or other signals capable of being received by a communications interface. These signals are provided to a communications interface via a communications path (i.e., channel) which carries signals and may be implemented using wire, cable, fiber optic, phone line, cellular link, RF, or other communications channels.

Part of the data generally stored in secondary memory 212 for access during digital front end operation is a set of translation tables that convert an incoming color signal into a physical machine signal.

This color signal can be expressed either as a colorimetric value; usually three components as L*a*b*, RGB, XYZ, etc.; into physical exposure signals for the four toners cyan, magenta, yellow and black. These tables are commonly created outside of the digital front end and downloaded, but are optionally created inside the digital front end in a so-called characterization step.

In the some of the descriptions below, specialty imaging elements are used in a dynamic pattern generation process to provide security features.

For example, a specialty imaging technique, as illustrated in FIGS. 5-8, create a pattern color space that incorporates specialty imaging features using standard page description language constructs, such as PostScript™ constructs. The pattern color space can be selected as a color for a color parameter for an object (e.g., lines, text, geometric shapes, freeform shapes, etc.) or an object characteristic (e.g., line color, fill color, foreground color, background color, etc.) in the document.

Specialty imaging techniques can be implemented by creating a specialty image object. Alternatively, specialty imaging techniques can be implemented using page description language constructs, such as PostScript™ constructs, to create a pattern color space, sometimes referred to as a "pattern ink." In other words, within page description languages, specialty imaging text and specialty imaging pattern inks can be implemented.

Rather than defining the specific string to be rendered at a specified location on the page, a specialty imaging string may be used to define a dynamically created pattern ink. This pattern ink is subsequently accessible by other page description language drawing and rendering commands through selection as a color parameter in the command.

Figure 5:
FIG. 5 shows an exemplary embodiment of a graphic image with certain objects printed with a pattern color space created using variable data.

With reference to FIG. 5, an exemplary graphic illustrates an exemplary embodiment of a process for dynamic creation of pattern inks. Through specialty imaging, the shirt, as well as the cart and the rails, can be changed into security elements on a variable data basis.

In this example, a "tile" of GlossMark™ text is defined as a pattern ink. This pattern ink can be previously designed with static characteristics. Alternatively, the pattern ink may be dynamically designed in conjunction with the processing of a corresponding print job. Both previously and dynamically-designed pattern inks can also incorporate variable data associated with the print job, as illustrated by the string "shirt" for the shirt (see FIG. 7) and "cart" for the cart (see FIG. 8). Additionally, the rails are rendered using a microtext string (see FIG. 8).

An exemplary embodiment of a pattern ink that includes a specialty imaging GlossMark™ test effect for the string "XEROX!"™ may be created using the following exemplary PostSript™ pseudo-code:

```
TABLE-US-00001 /GlossFont /NeueClassic-GL-24 def
        /GlossFontsize 28.8 def
        /GlossFontstring (XEROX!) def
        %% this sets the Font parameters.
            /PatternType 1
        %% tiling properties can be defined similar to Holladay dots
            /BBox [0 0 GlossFontstring stringwidth pop GlossFontsize]
            /XStep GlossFontstring stringwidth pop
            /YStep smallfontsize
        %% geometric values for the tiling rectangle
            /PaintProc { 0 0 moveto GlossFontstring show
            }
        %% this creates the variable data string defined through
        GlossFontstring matrix makepattern
        /GlossTextPaint exch def
        %% identifying the patterns as GlossTextPaint
```

Figure 6:
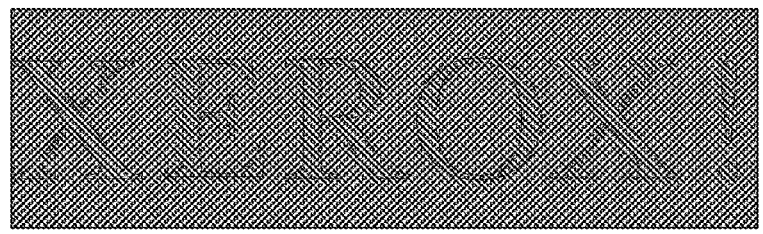
FIG. 6 shows an exemplary embodiment of a pattern color space created using variable data.

FIG. 6 shows the exemplary pattern ink (or pattern color space) created by the PostSript™ pseudo-code listed above. The string "XEROX!"™ can be traced as the texture change of the halftone for this pattern ink. In this example, the pattern color space of FIG. 6 is available as a "color" or "ink" selection for subsequent PostScript™ drawing commands. Note that the geometry and size of the pattern in FIG. 6 may be characterized as a fixed portion of the pattern ink. In the example above, the geometry and size of the pattern is created in the first step of the pseudo code.

In one embodiment, a pattern ink (or pattern color space) used for tiling is defined with respect to an origin of a page (i.e., the pattern ink is available for all objects on the page, except for image objects) and not with respect to a specific object.

For example, this means that the GlossMark™ text inside the shirt may start with the letter "X" or any other letter of the string depending on the location of the object in relation to the page. In other words, two identical shirts, drawn at different locations on the page may have different internal Gloss-Mark™ patterns, since their starting position varies.

Figure 7:
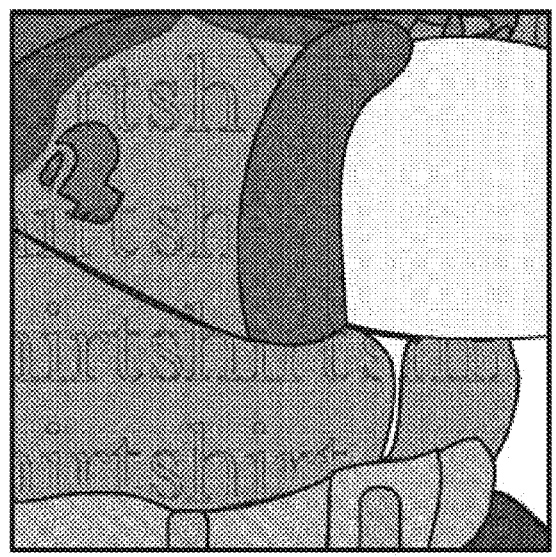
FIG. 7 shows a portion of the graphic image of FIG. 5 with an object filled with the pattern color space of FIG. 6.

With reference to FIG. 7, the pattern ink of FIG. 6 is used as the fill color for the shirt of FIG. 5 using the word "shirt" as the variable data string (rather than "Xerox!")™. In other words, the word "shirt" is used as GlossMark™ text to create the pattern ink used to render the shirt area of FIG. 5. The word "shirt" is tiled with respect to other occurrences of the word which is based on the tile size for the pattern ink.

Figure 8:
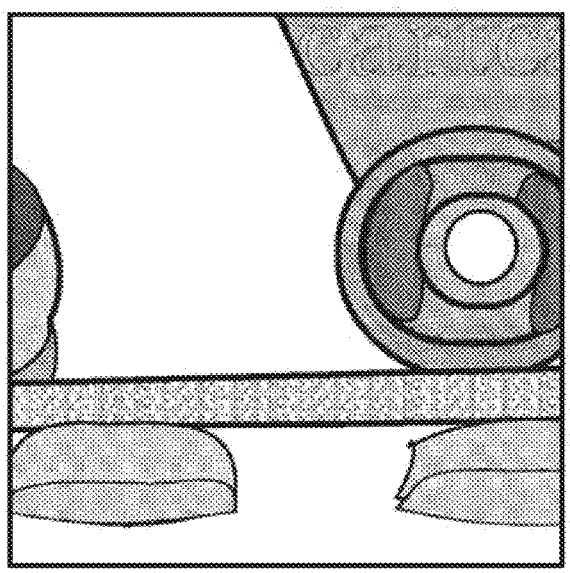
FIG. 8 shows another portion of the graphic image of FIG. 5 with another object filled with another exemplary embodiment of a pattern color space using variable data.

Multiple pattern inks can be defined. For example, a pattern consisting of lines of microtext may be defined and used to render the rails at the bottom of the graphic. FIG. 8 provides an enlargement of a small area of the rails to show this pattern ink with microtext.

As previously noted, specialty imaging techniques may be text based, wherein text is any symbol that is encapsulated as font, or image based. In the conventional specialty imaging techniques, the text based specialty imaging techniques can be realized in real-time, whereas the image-based conventional specialty imaging techniques are performed as an offline process, eliminating any real-time capabilities, because of the computational requirement for images that cannot easily be done inside a Postscript™ dataflow through a digital front end.

In the conventional specialty imaging techniques, pattern inks in page description languages; such as PostScript™ and PDF (Portable Document Format); are typically used for repeating patterns, essentially, the pattern inks correspond to tiles that are regularly laid across the page.

In a typical situation, each pattern ink is a rectangular area that is repeated in both x-direction and y-direction across the page. Subsequent PostScript™ commands 'expose' that pattern to the printed page in the desired spots, where the phasing of the pattern ink is constant with respect to the original definition.

For example, by defining two pattern inks that have the same average visual color (say in Lab space) but very distinct toner combinations, variable data (text-based) UV fluorescence specialty imaging can be realized.

In this example, the background is 'painted' with one of the pattern inks and the foreground with the other, resulting in a distinct UV fluorescence. In essence, the components of the specialty imaging effect are loaded into distinct pattern inks and subsequently selectively 'paint' with these two components.

For an image-based real-time specialty imaging technique, the approach described above needs to be inverted. In other words, the image is loaded into the pattern ink memory. This leads to a single pattern ink.

More specifically, the image based real-time specialty imaging technique uses a specialty imaging font (such as a GlossMark™ font or CorrelationMark™ font) in conjunction with the variable data string and uses the image as the "paint" that is poured through the specialty imaging font.

It is noted that the various features of the process disclosed herein may be implemented using hardware, software, or firmware in any suitable combination.

The image based real-time specialty imaging technique process for processing a print job begins when the print job, including variable data to be used in conjunction therewith, in a page description language is received at a digital front end associated with a printing system. At least one object within the print job includes a specialty imaging font (such as a GlossMark™ font or CorrelationMark™ font) that provides fraud protection for printed materials resulting from the print job.

A pattern color space is created using the actual image of the print job so that such that the specialty imaging font (such as a GlossMark™ font or CorrelationMark™ font) is painted with the pattern color space in a tiling manner. In other words, a data string is created using the specialty imaging font (such as a GlossMark™ font or CorrelationMark™ font) and the specialty imaging font data string is painted with the actual image of the print job.

The image based real-time specialty imaging technique process for processing a print job creates a GlossMark™ or CorrelationMark™, in real-time, by: defining, in the page description language, a variable portion; defining, in the page description language, a fixed portion of the pattern color space.

The fixed portion is the image of the print job; defining, in the page description language, a bounding shape for the pattern color space; and defining, in the page description language, a procedure for painting the variable and fixed portions within the bounding shape, with the image of the print job. The variable portion may be based in part on variable data associated with the print job. The fixed portion ("paint") is the image of the print job.

The variable data string that is created using the specialty imaging font (such as a GlossMark™ font or Correlation-Mark™ font) is painted with the image of the print job, wherein specialty imaging effects in the specialty imaging font is used to create the GlossMark™ or CorrelationMark™, with the image being used as the paint, instead of using two different pattern inks to create the GlossMark™ or Correla-tionMark™.

In implementing the image based real-time specialty imaging technique and creating a variable data string, the process does not know, in advance, what the string is going to be used.

Additionally, if the size of the font (in pixels) is compared with the size of the image, the selected image is not typically exactly N-lines high and M-characters wide.

Figure 9:
FIG. 9 is an exemplary embodiment of a process for creating a pattern color space for use in conjunction with processing a print job.

In order to circumvent this situation, a single pattern ink cell white space is created on the top and side of the pattern cell, as illustrated in FIG. 9. Preferably, the single pattern ink cell white space is created only once and is placed in a pattern cache for performance.

It is noted that it is not important on which sides the white space is created as long as it is created in both the vertical and horizontal direction since the "pattern" of FIG. 9 is tiled across the entire page, and thus, the white space will be all around the image.

The required size of the white space can be calculated from the specialty imaging font's properties. With respect to the vertical direction (320 of FIG. 9) the line-height of the specialty imaging font is utilized as the height 320 of the white space. Through the tiling, the image based real-time specialty imaging technique will create a full line of white space above and below the image.

When writing the variable data string with the effect, the ceiling {imageheight/lineheight} is the number of lines of variable data text. If the variable data text string does not extend across this range, the image based real-time specialty imaging technique can (a) fill the remainder with a blank " " character or preferably (b) replicate the string.

The horizontal white space (310) can be determined by two different scenarios.

In the first scenario, the image based real-time specialty imaging technique deals with strings that physically fit into image size. An upper bound to the white space would be the image width parameter.

It is noted that the upper bound could be extended by the known string length limitations [variable data field length association].

In a second scenario, the image based real-time specialty imaging technique adds additional white space to the side of the image (essentially the remainder of the page). This is utilized when the expected string is completely unknown.

Once the pattern ink (FIG. 9) is created, the pattern ink is now used as a "paintbrush" to actually render the variable data text. In contrast to all previous specialty imaging approaches, the image based real-time specialty imaging technique uses the specialty imaging effect embedded in the delivered fonts and use the pattern ink (FIG. 9) as the "constant" part of the method.

An exemplary embodiment of specialty imaging effects in the specialty imaging font being used to create the Gloss-Mark™ or CorrelationMark™, with the image being used as the paint, may be created using the following exemplary PostSript™ pseudo-code:

```
% creates a pattern ink from an image and whitespace
% xpix ypix = pixels lines of image
% xsize ysize = size of image
% xmargin ymargin = white space
<<
  /PatternType 1
  /PaintType 1
  /TilingType 1
  /BBox [xmargin ymargin xsize xmargin add xgap add ysize
  ymargin add ygap add]
```

-continued

PostSript™ pseudo-code:

```
  /XStep xsize xgap add
  /YStep ysize ygap add
  /PaintProc
  {
    [xsize 0 0 ysize xmargin ymargin] concat
    /ImageDict 8 dict def
    ImageDict begin
      /ImageType 1 def
      /Width x def
      /Height y def
      /BitsPerComponent 8 def
      /ImageMatrix [xpix 0 0 –ypix 0 ypix] def
      /DataSource imgFile def
      /Decode [ 0 1 0 1 0 1 ] def
    end
    COLORSPACE setcolorspace
    ImageDict image
    imgFile resetfile
  }
>>
matrix
makepattern setpattern
% fs = font height
/lines ysize fs div ceiling cvi def
/NeueSecurity-Bold-CR-36 fs selectfont
% write enough lines to create entire image
lines
{
  x y fs DEC mul sub moveto
  str show
  /y y fs add def
} repeat
```

Figure 10:
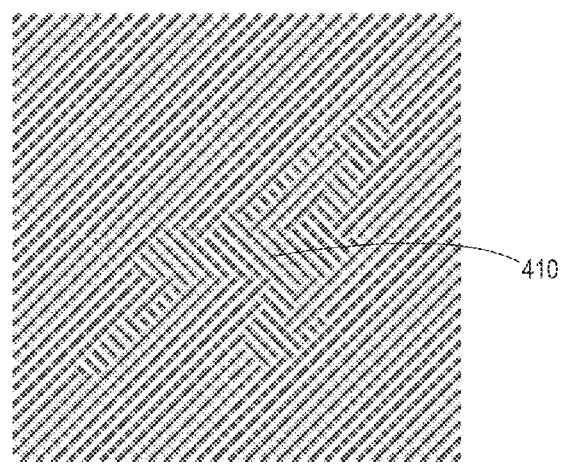
FIG. 10 shows a 'typical' GlossMark™ font element.

Variable or personalized data is then written using the pattern ink using CorrelationMark™ or GlossMark™ fonts. FIG. 10 shows a 'typical' GlossMark™ font element (in this case the letter "A" (410)).

Figure 11:
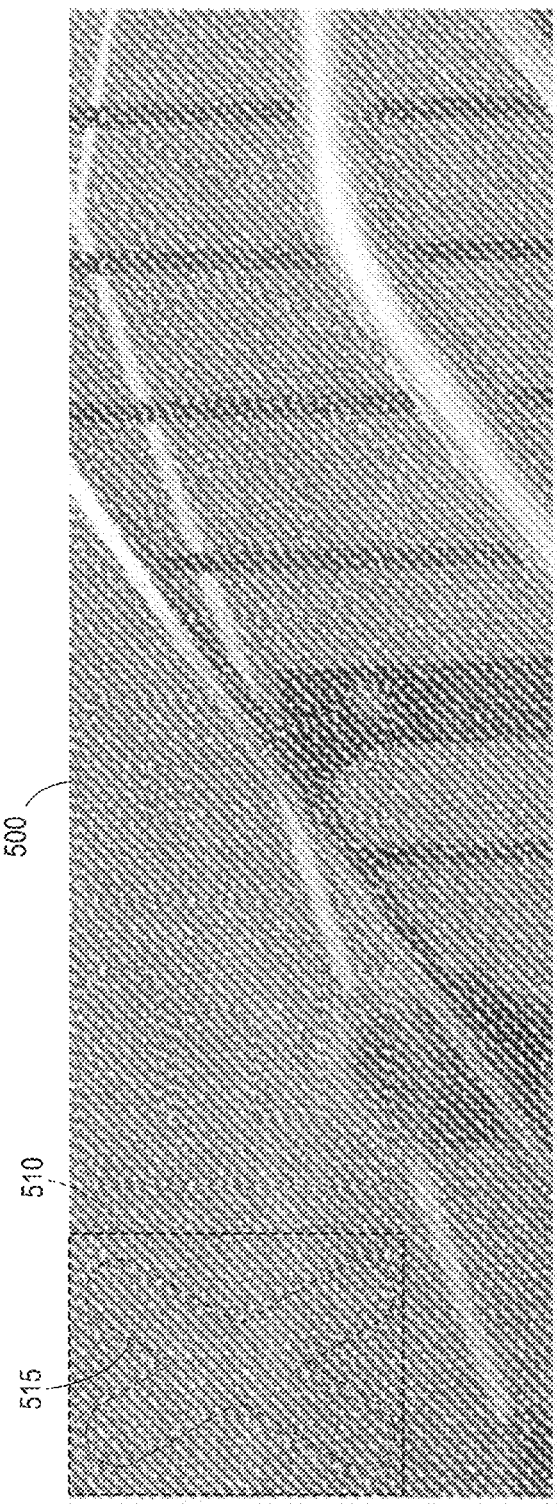
FIG. 11 shows an example of a CorrleationMark™ string.
Figure 12:
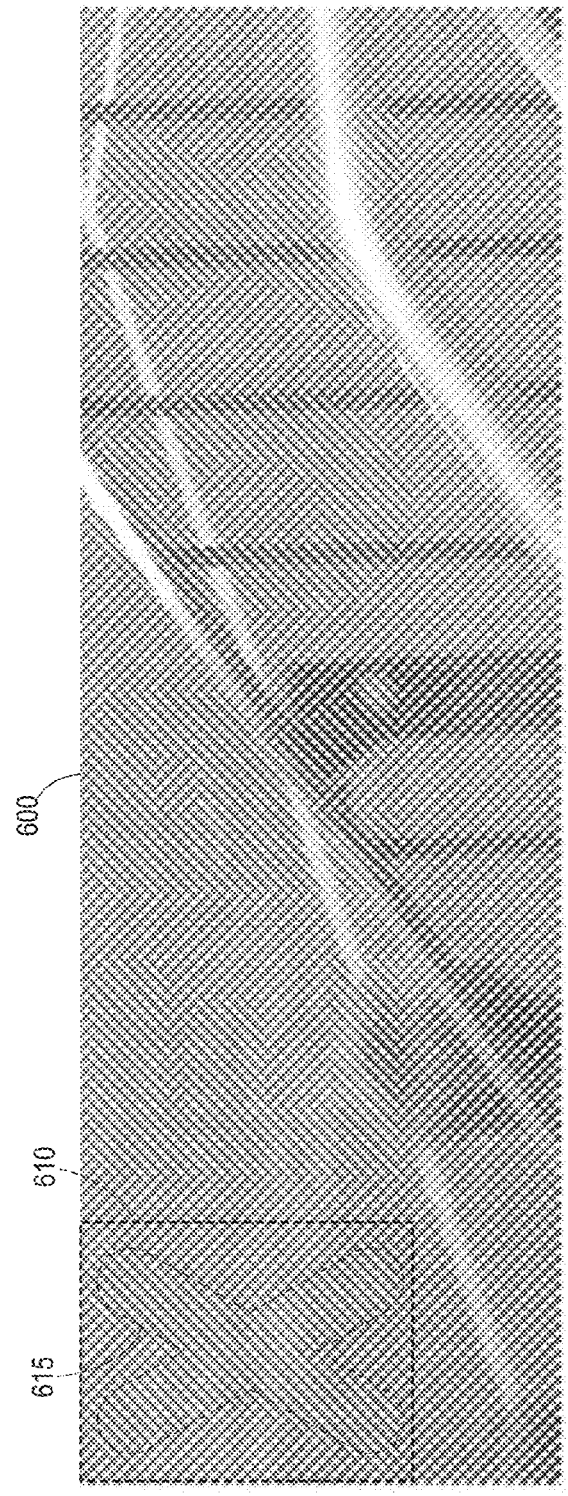
FIG. 12 shows an example of a GlossMark™ string.

FIGS. 11 and 12 show magnified portions (500 and 600) of a CorrleationMark™ and GlossMark™ string (XEROX)™, respectively, printed using the same image as the pattern ink (FIG. 9). The internal structure, that the specialty imaging effect and the text have maintained, is clearly visible.

More specifically, in FIG. 11, the dotted box 510 encloses the letter X (which has been traced 515) of the Corrleation-Mark™ string (XEROX)™. In addition, in FIG. 12, the dotted box 610 encloses the letter X (which has been traced 615) of the GlossMark™ string (XEROX)™.

It is noted, from FIGS. 11 and 12, that the available dynamic range of the image is lost since all areas have maintained a certain percentage of "white space" for the specialty imaging effect.

Moreover, it is noted that the images turn 'lighter' than the image would have been printed in the normal path due to the additional white space. However, the darkness adjustment can be performed in an offline step. In addition, the darkness can be approximately adjustment by using a simple data scale inside the PostScript™ data.

An example of providing specialty marks is the use of color shifting ink, which appears as one color from a certain angle and another color from another angle. Conventionally, color shifting required a special ink or marking material.

To avoid the use of special inks or marking materials, the color shifting result may be realized by creating a pattern of two different colors, wherein each color has a different height and at least one of the colors is created with a very thin line; for example, one pixel width line.

Figure 13:
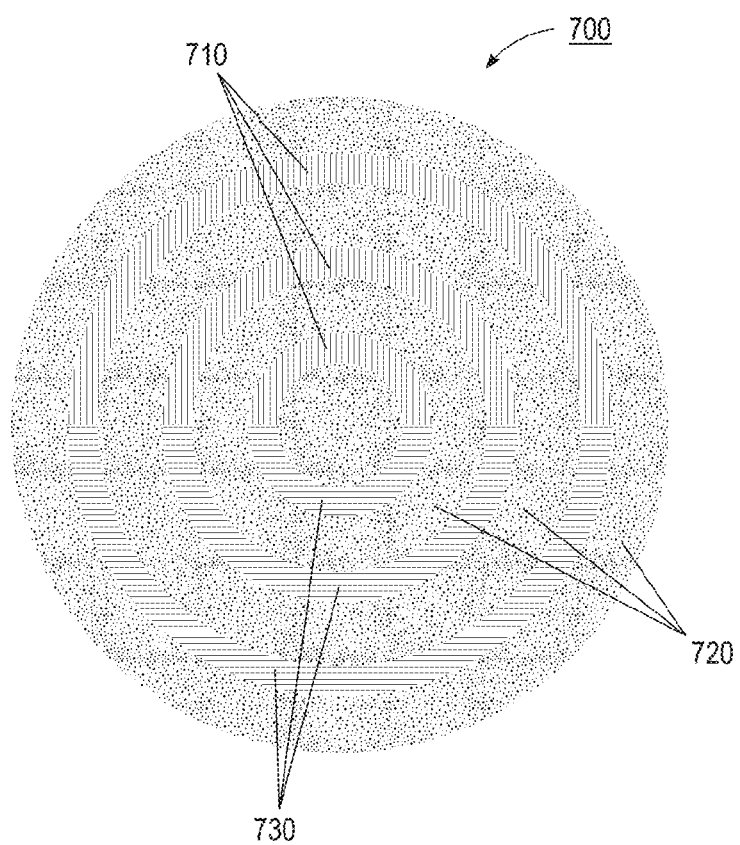
FIG. 13 shows an example of a color shift ink image using non-special inks or marking materials.

It is noted, as illustrated in FIG. 13, that there is color shift with 710/720 and 730/720, but not if just 710/730. The intersection of 710/730 creates the distinct line which virtually disappears when shifting.

For example, as illustrated in FIG. 13, a color shifting image 700 can be created using two colors 710 and 730. Each of the colors 710 and 730 has a marking material height, H1. The color shifting image 700 further includes a third color 720 which has a marking material height, H2, wherein the marking material height, H2, is greater than the marking material height, H1.

In one example, the two colors 710 and 730 may be cyan (C) and magenta (M), while the third color 720 may be a composite black such that the color 720 is composed of 100% black (K) and 50% of cyan (C), magenta (M), and yellow (Y). The composite black (third color 720) would have marking material height, H2, which is 2.5 times greater than the marking material height, H1.

It is noted that in the example of FIG. 13, the high color black 720 is wider than the low colors 710 and 730 (cyan and magenta). The smallest magenta or cyan square may be one pixel.

It is further noted that the reverse, where the low color is wider than the high color does not result in a color shift.

It is noted that the color shift may go from black and magenta to black, whereas conventional US currency goes from gold to green.

It is also noted that the low color may be created using a single color component marking material; a single color marking material may be cyan colored marking material (toner), magenta colored marking material (toner), or yellow colored marking material (toner). When the low color is created using a single color component marking material, the background of the color shifting region may be initially rendered with the single color component marking material associated with the low color. Thereafter, the high color can be rendered, in the color shifting region, over the rendered background so as to create the marking material height difference between the low color and the high color.

If the low color is created using more than one single color component marking material, the background of the color shifting region may be initially rendered with the single color component marking materials associated with the low color. Thereafter, the high color can be rendered, in the color shifting region, over the rendered background so as to create the marking material height difference between the low color and the high color.

As noted above, in the area of security printing, documents are protected from copying, forging, and counterfeiting using multiple techniques. Specialty Imaging is one such method of security printing which uses standard materials, such as papers, inks, and/or toners.

MicroGloss (or Artistic Black for VIPP) is a Specialty Imaging technique, which does not require a special tool; e.g., UV light to view and is especially strong in anti-copying.

MicroGloss uses a pair of colors which appear about the same when viewing straight on but show a differential gloss when the image is tilted due to the pile height of the toner or ink.

MicroGloss can also be used to create two micro gloss layers such that only the first micro gloss layer is visible when viewing the image straight on, and the second micro gloss layer is viewable upon tilting the image. It is noted that upon tilting the image the first micro gloss layer is no longer visible.

To create a two layered micro gloss image, one pattern ink with a MicroGloss color pair and variable data is created, and then a second pattern ink with a visibly different MicroGloss color pair but the same variable data is created.

The background of the image is written with the first pattern ink followed by the second layer with the second pattern ink and different variable data.

Figure 14:
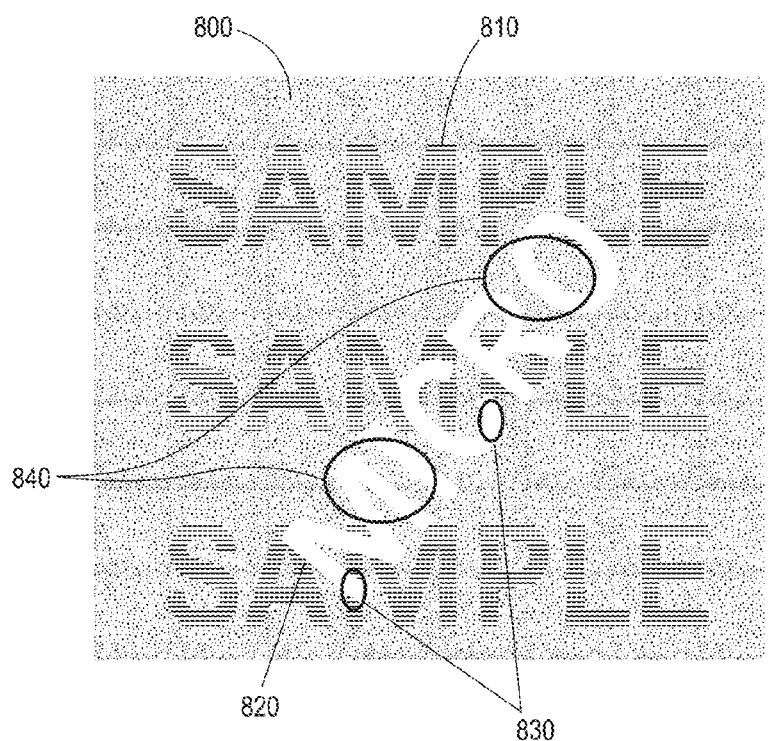
FIG. 14 shows an example of a double layer micro gloss image.

As illustrated in FIG. 14, the first ink pattern may be composed Color1-High 800 (such as black hi) and Color1-Low 810 (such as black low) with variable data "SAMPLE."

As illustrated in FIG. 14, the second ink pattern may be composed of Color2-High (such as brown high) and Color2-Low (such as brown low) with variable data "SAMPLE." The second ink pattern is used to paint variable data "MICRO."

Upon rendering this image, the variable data "SAMPLE" is rendered in Color1-Low 810 and the background is rendered in Color1-High 800; however, where the portions of the variable data "MICRO" overlap the variable data "SAMPLE," the overlapping portions (within ovals 830) are rendered with Color2-Low, and where the portions of the variable data "MICRO" overlap the background, the overlapping portions (within ovals 840) are rendered with Color2-Hi.

In the example discussed above, the rendered image would include a black hi background with black low "SAMPLE." The rendered image would also include brown low portions (within ovals 830) where portions of the variable data "MICRO" overlap the variable data "SAMPLE," and brown hi portions (within ovals 840) where the portions of the variable data "MICRO" overlap the background.

It is noted that hi/low color pair may be dark red or any of the hi/low color pairs identified in co-pending U.S. patent application Ser. No. 13/776,868, filed on Feb. 26, 2013. The entire content of co-pending U.S. patent application Ser. No. 13/776,868 is hereby incorporated by reference.

It is also noted that gloss marks are not scalable because gloss marks require a new font for each font size. Moreover, MicroGloss only works at small sizes.

Thus, it is desirable to realize a scalable gloss effect.

Such a scalable gloss effect can be realized by rendering one region with a relatively smooth surface while rendering another region with a relatively rougher surface. The appearances of the two surfaces are approximately the same at one angle, while giving a gloss effect; e.g., text or graphics; at another angle.

Figure 15:
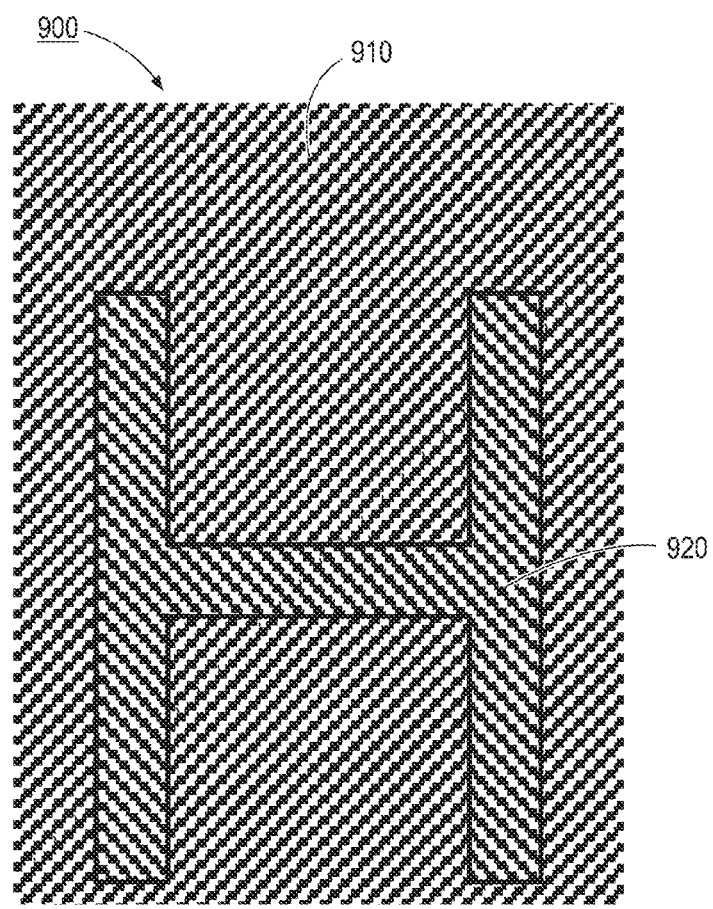
FIG. 15 shows an example of a gloss mark.

Gloss marks, as shown in FIG. 15, create a gloss effect by using two different halftone patterns 910 and 920. As illustrated in FIG. 15, the background is rendered using a first halftone pattern 910 and the letter H is rendered using a second halftone pattern 920. To a casual observer, the image 900 will appear as one color and pattern at one angle, while the character "H" can be seen when tilted. In other words, the H appears to the casual observer as being drawn into the image when the image is tilted.

Figure 16:
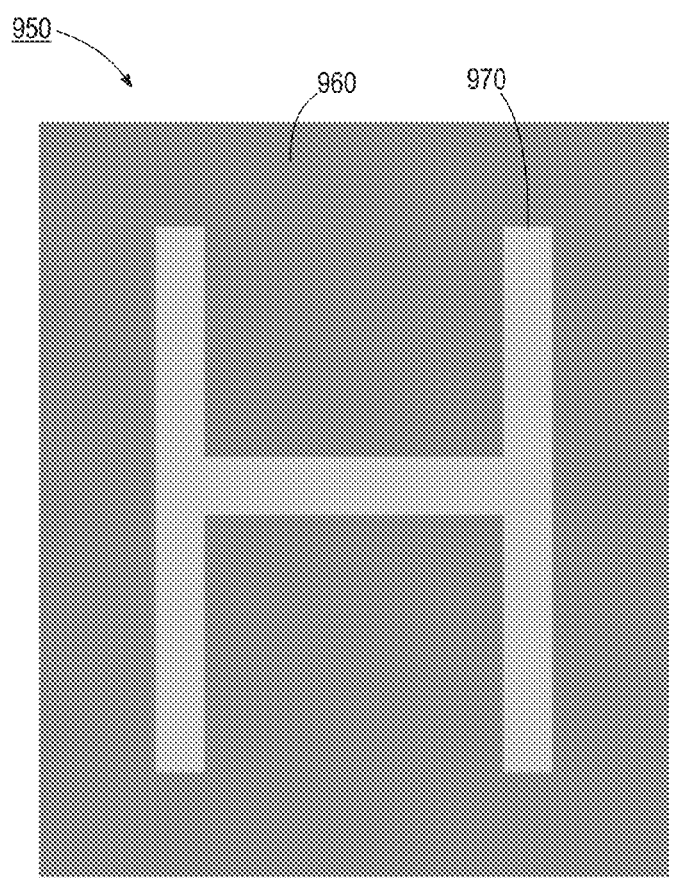
FIG. 16 shows an example of a micro gloss mark.

MicroGloss, as illustrated in FIG. 16, creates a gloss effect by using two different ink or toner pile heights. To a casual observer the image 950 will appear as one color 960 at one angle, while the gloss character 970 can be seen when tilted.

Figure 17:
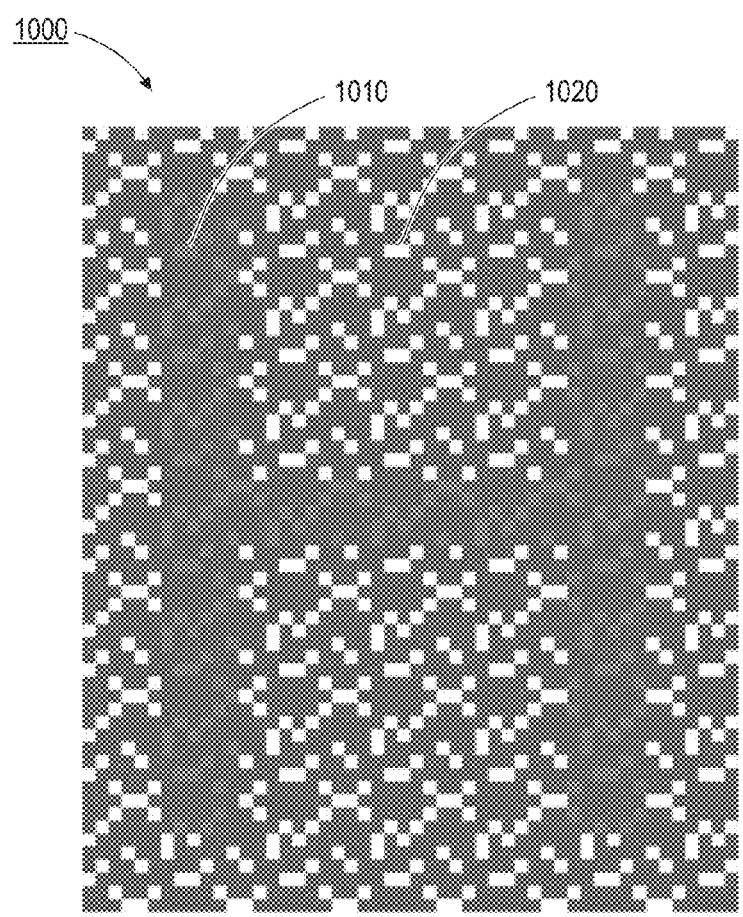
FIG. 17 shows an example of the gloss effect when using two different patterns with one relatively smoother than the other.

As illustrated in FIG. 17, a gloss effect is created by using two different patterns with one pattern being relatively smoother than the other pattern. In FIG. 17, the "H" is smoother as compared to the background.

In addition, as illustrated in FIG. 17, the "H" has yellow color holes (1010) and compared to no color (white) holes (1020) in the background. It is noted that clear toner would be used in place of yellow if available.

To a casual observer the image 1000 will appear as one color and pattern at one angle, while the character "H" can be seen when tilted. It is noted that this gloss effect is scalable.

To create the gloss effect of FIG. 17, one pattern ink is created with white holes and a second pattern ink is created with yellow holes. Thereafter, a text box is created with a certain background color (such as magenta) and white holes (1020) are added. The letter, "H," is then written and yellow dots (1010) are added.

Figure 18:
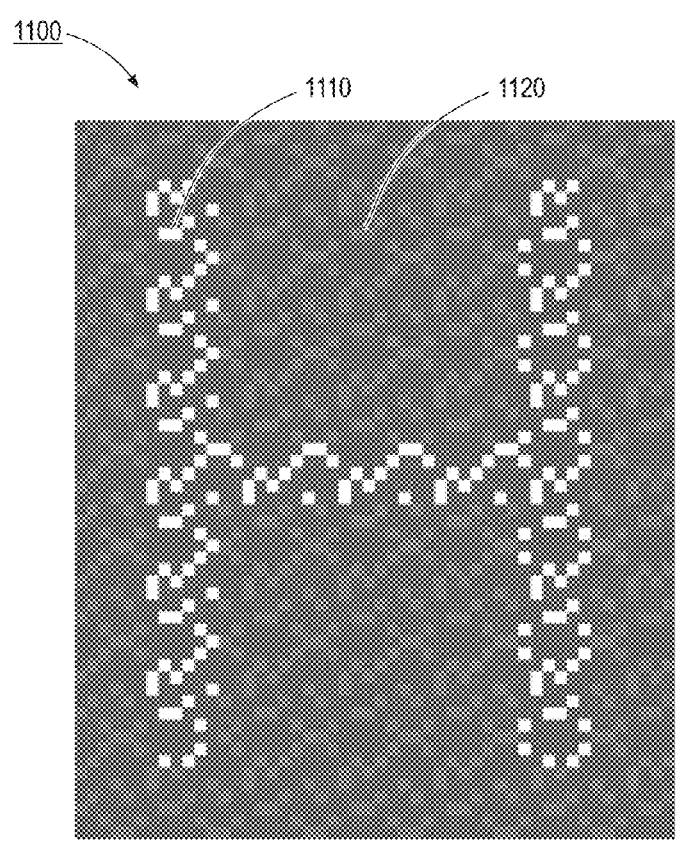
FIG. 18 shows an example of the reverse gloss effect of FIG. 17.

As illustrated in FIG. 18, a reverse gloss effect is created by using two different patterns with one pattern being relatively smoother than the other pattern. In FIG. 18, the background is smoother as compared to the "H."

In addition, as illustrated in FIG. 18, the "H" has white color holes (1110) and compared to yellow holes (1120) in the background. It is noted that clear toner would be used in place of yellow if available.

To create the gloss effect of FIG. 18, one pattern ink is created with white holes and a second pattern ink is created with yellow holes. Thereafter, a text box is created with a certain background color (such as magenta) and yellow holes (1220) are added. The letter, "H," is then written and white dots (1110) are added.

Figure 19:
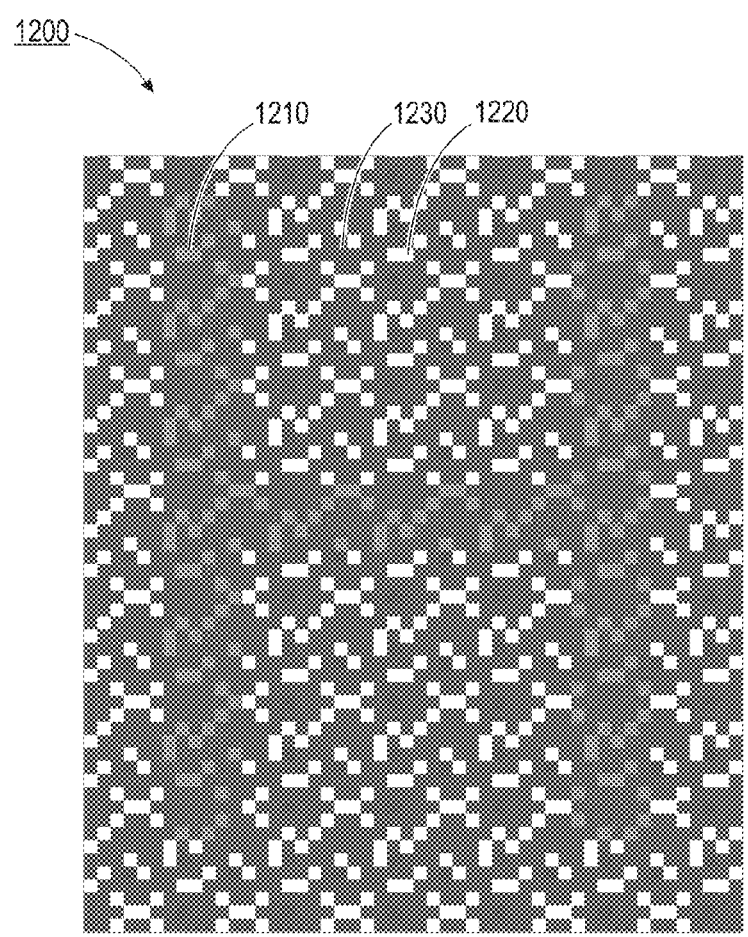
FIG. 19 shows the example of FIG. 17 with the addition of darker pixels.

It is noted that a better color match can be realized by adding darker pixels 1230, as illustrated in FIG. 19. In FIG. 19, the "H" has yellow color holes (1210) and compared to no color (white) holes (1220) in the background, as well as, darker pixels 1230 in the background.

Specialty Imaging techniques often rely on creating metameric pattern ink pairs such as UV (ultraviolet)/florescence and IR (infrared). The scalable gloss effect, described above, used a pair of pattern inks that appear about the same at one angle and show a differential gloss effect when tilted.

It is noted that Specialty Imaging quality is judged on the strength of the effect; e.g., UV signal and the hiding between the foreground and background pattern inks. In other words, the test is whether the signal (pattern) that is seen under UV illumination can be seen under ambient illumination. Conventionally, distraction patterns, color compensation, and/or noise have been used to help in hiding, but at the cost of effect (signal) degradation.

Figure 20:
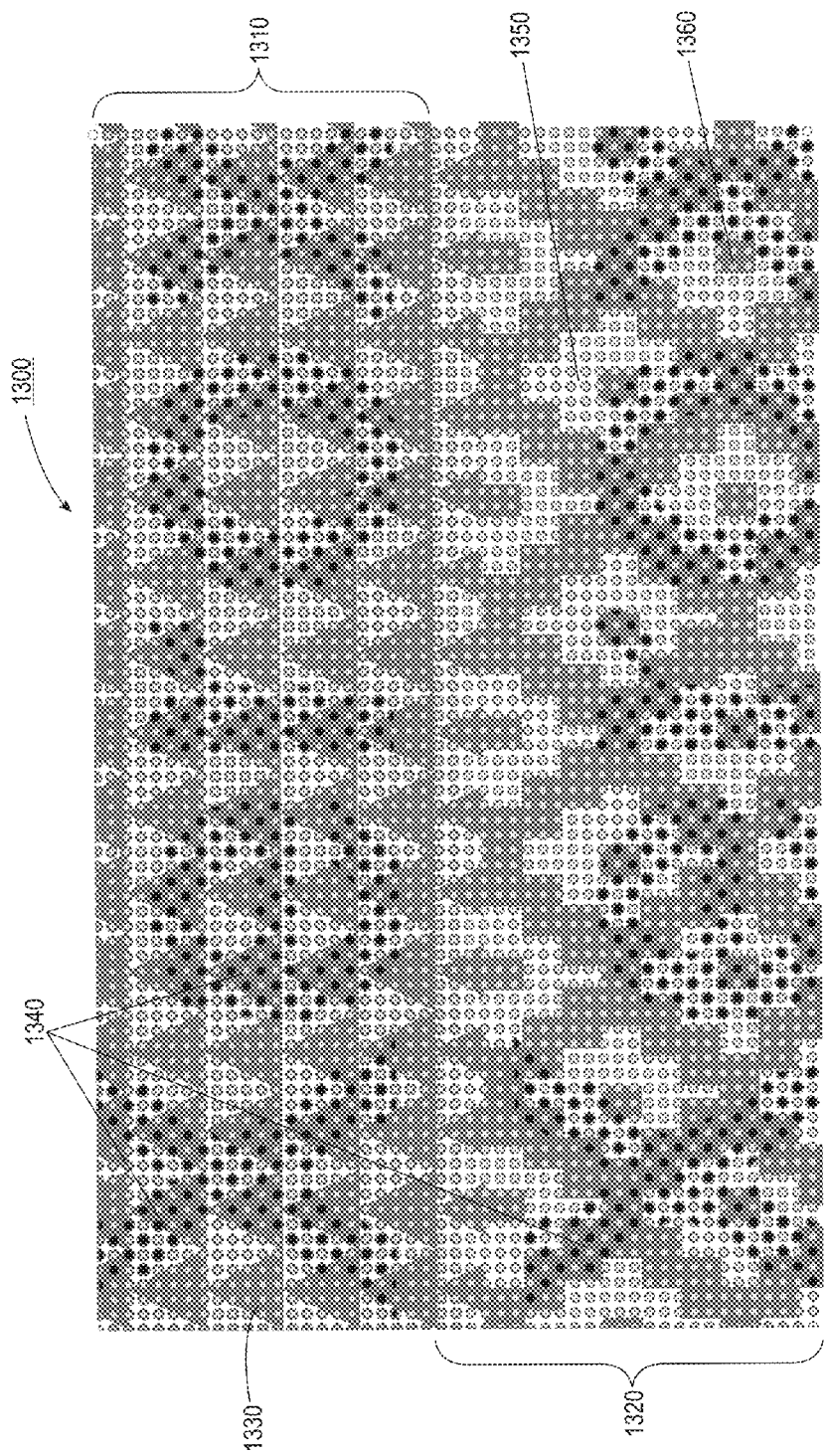
FIG. 20 shows an UV/florescence example of adding both a structure and color to an image to improve the color matching.

As illustrated in FIG. 20, an example of an UV (ultraviolet)/florescence effect is created by adding both a structure and color to enhance the hiding between the foreground and background pattern inks.

In this example, as illustrated in FIG. 20, the structure in the top half (1310) of the image 1300 is a triangle 1330. The triangle structure 1330 is in both the foreground and the background.

The background pattern ink colors may be cyan, magenta, and yellow while the foreground pattern ink colors may be red, blue, white, yellow, and magenta.

As illustrated in FIG. 20, the top half (1310) of the image 1300 includes the string "Xerox"™.

The structure in the bottom half (1320) of the image 1300 is a diamond 1350 and a small square 1360 at its center. The diamond 1350 and small square 1360 structure is in both the foreground and the background.

As illustrated in FIG. 20, the bottom half (1320) of the image 1300 includes the string "Xerox"™.

To enhance Specialty Imaging quality, color substrates are used in conjunction with Specialty Imaging color matching techniques, wherein at least one of the pattern inks has holes allowing the substrate color to show through.

To enhance quality, the substrate color that shows is matched in the other pattern ink by reproducing the same color via available markers, thereby realizing improved color matching (or better hiding) between the foreground and background pattern inks with little or no degradation in effect.

As noted above, to enhance quality, the substrate color that shows is matched in the other pattern ink by reproducing the same color via available markers.

Figure 21:
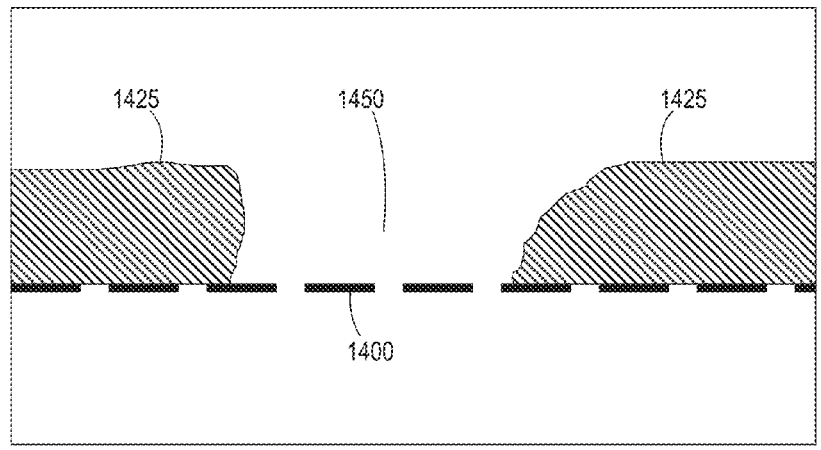

In realizing this enhancement, as illustrated in FIG. 21, one pattern ink allows the color of the substrate 1400 to be viewed via holes 1450 in the pattern ink 1425. The other pattern ink, as illustrated in FIG. 22, fills these holes with the matching color marker 1475.

The pattern inks appear almost identical in color but exhibit differential properties in other areas, such as gloss effect.

This allows improved color consistency between the foreground and background pattern inks currently used in UV/florescence, IR, and gloss effects.

Figure 22:
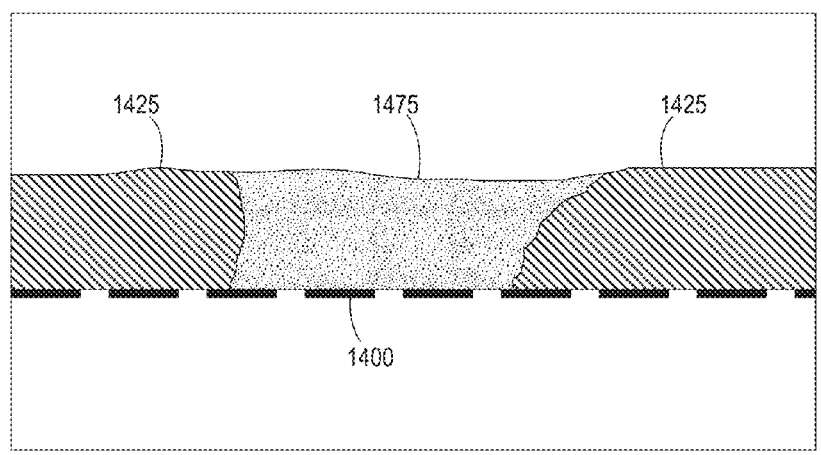
FIG. 22 shows a portion of a printed image having a hole to allow substrate show through wherein the hole is filled with a marking material matching the color of the substrate.

FIGS. 21 and 22 demonstrate the use of a colored substrate 1400 with a same color marker 1475.

FIG. 21 shows a colored (color1) substrate 1400 with black markers 1425 on both sides and no marker in the center (hole 1450). This example pattern ink shows colors black/color1/black, wherein color1 is from the substrate.

FIG. 22 appears the same color as FIG. 21, but has a difference in that color1 is from a marker. This difference can be used to create security elements such as UV markers.

In the cases where the substrate does not match a primary marker color in the printer, the appropriate mix of marker materials filling the holes can be used to achieve color consistency.

It is further noted that a comparison of images using holes showing yellow substrate and holes filled with yellow marker verses using holes showing white substrate and holes filled with yellow ink, the gloss effect works in all cases.

However, the color matching is improved when the holes are filled with a marking material, preferably a marking material matching the color of the substrate, by making it more difficult to read the text when the substrate is not tilted.

In summary, the use of a color substrate and matching color marker enhances Specialty Imaging quality. The color of the substrate shows through holes in one pattern ink, while the corresponding holes in another pattern ink are filled with a color marker matching the color of the substrate.

The differential properties between the filled and unfilled holes are used to create Specialty Imaging effects such as gloss and UV.

More specifically, if the holes are filled with a marking material having a color matching the color of the substrate upon which the image is being rendered, a gloss effect is realized.

If the holes are filled with a marking material having a color matching the color of the substrate upon which the image is being rendered, a UV effect is realized by the fluorescents in the recording medium or substrate showing through the holes.

It is further noted that a copier or scanner also views the substrate color and marker filled holes the same for superior anti-copy properties.

For example, if the image illustrated in FIG. 18 was rendered on a substrate having a color matching the color of the marking material associated with holes 1120, a copier or scanner would view the image illustrated in FIG. 18 as a solid color, not discerning the "H."

In summary, a method for rendering a color shift image pattern on a recording medium creates, in a pre-defined image region, an image pattern including a first pattern having a first color and a second pattern having a second color, the first pattern having a width smaller than the second pattern, the first color being different from the second color; and renders, using marking materials, the image pattern on a recording medium, a height of the marking materials used to render the second color being higher than a height of the marking materials used to render the first color such that the first pattern and the second pattern are visible when a relative angle between an observer's viewing angle and an angle of illuminating the recording medium by an illumination source is a first angle, and the first pattern is not visible when the relative angle between the observer's viewing angle and the angle of illuminating the recording medium by the illumination source is a second angle, the second angle being not equal to the first angle.

The width of the first pattern may be a pixel wide. The method first color may correspond to a single color component marking material.

The image pattern may include a third pattern having a third color; the third pattern having a width smaller than the second pattern the third color being different from the second color; and a height of the marking materials used to render the second color is higher than a height of the marking materials used to render the third color such that the first pattern, the second pattern, and the third pattern are visible when the relative angle between the observer's viewing angle and the angle of illuminating the recording medium by the illumination source is the first angle and the third pattern is not visible when the relative angle between the observer's viewing angle and the angle of illuminating the recording medium by the illumination source is a third angle, the third being not equal to the first angle.

The width of the third pattern may be a pixel wide. The third color may correspond to a single color component marking material.

The height of the marking materials used to render the second color may be greater than 1.8 times higher than the height of the marking materials used to render the first color.

The height of the marking materials used to render the second color may be greater than 1.8 times higher than the height of the marking materials used to render the third color.

A system for rendering a color shift image pattern on a recording medium includes a processor for creating, in a pre-defined image region, an image pattern including a first pattern having a first color and a second pattern having a second color, the first pattern having a width smaller than the second pattern, the first color being different from the second color; and a print engine for rendering, using marking materials, the image pattern on a recording medium. The print engine deposits, on the recording medium, the marking materials used to render the first color, the deposited marking materials used to render the first color having a first height. The print engine deposits, on the recording medium, the marking materials used to render the second color, the deposited marking materials used to render the second color having a second height, the second height being higher than the first height such that the first pattern and the second pattern are visible when a relative angle between an observer's viewing angle and an angle of illuminating the recording medium by an illumination source is a first angle, and the first pattern is not visible when the relative angle between the observer's viewing angle and the angle of illuminating the recording medium by the illumination source is a second angle, the second angle being not equal to the first angle.

The width of the first pattern may be a pixel wide. The method first color may correspond to a single color component marking material.

The processor may create, in the image pattern, a third pattern having a third color; the third pattern having a width smaller than the second pattern, the third color being different from the second color; and the print engine may deposit, on the recording medium, the marking materials used to render the third color, the deposited marking materials used to render the third color having a third height, the second height being higher than the third height such that the first pattern, the second pattern, and the third pattern are visible when the relative angle between the observer's viewing angle and the angle of illuminating the recording medium by the illumination source is the first angle and the third pattern is not visible when the relative angle between the observer's viewing angle and the angle of illuminating the recording medium by the illumination source is a third angle, the third being not equal to the first angle.

The width of the third pattern may be a pixel wide. The third color may correspond to a single color component marking material.

The second height may be greater than 1.8 times higher than the first height. The second height may be greater than 1.8 times higher than the third height.

A recording medium includes a substrate; and marking materials formed on the substrate. The marking materials form, on the substrate, a first pattern having a first color; and a second pattern having a second color, the first color being different from the second color. The marking materials forming the first pattern having the first color has a first width. The marking materials forming the second pattern having the second color has a second width, the first width being smaller than the second width. The marking materials forming the first pattern having the first color has a first height. The marking materials forming the second pattern having the second color has a second height, the second height being higher than the first height such that the first pattern and the second pattern are visible when a relative angle between an observer's viewing angle and an angle of illuminating the recording medium by an illumination source is a first angle, and the first pattern is not visible when the relative angle between the observer's viewing angle and the angle of illuminating the recording medium by the illumination source is a second angle, the second angle being not equal to the first angle.

The first width may be a pixel wide. The first color may correspond to a single color component marking material. The second height may be greater than 1.8 times higher than the first height.

A method for rendering double layer micro gloss image pattern on a recording medium, electronically creates a first electronic pattern ink, the first electronic pattern ink including a first color pair and a first pattern, the first color pair including a first high color and a first low color; electronically creates a second electronic pattern ink, the second electronic pattern ink including a second color pair and the first pattern, the second color pair including a second high color and a second low color, the second color pair being visibly different from the first color pair; electronically creates a first layer in an electronic image region by electronically painting the electronic image region using the first electronic pattern ink; electronically creates a second layer in the electronic image region by electronically painting, using the second electronic pattern ink, a second pattern; and renders, using marking materials, the electronic image region on a recording medium such that the when the first pattern is visible, the second pattern is not visible and when the second pattern is visible, the first pattern is not visible.

The first low color may correspond to a single color component marking material. The first high color may be black hi and the first low color may be black low. The second high color may be brown hi and the second low color may be brown low. The first high color may be dark-red hi and the first low color may be dark-red low.

The first structure may be different from the second structure.

A system for rendering double layer micro gloss image pattern on a recording medium includes a processor for electronically creating a first electronic pattern ink, the first electronic pattern ink including a first color pair and a first pattern, the first color pair including a first high color and a first low color. The processor electronically creates a second electronic pattern ink, the second electronic pattern ink including a second color pair and the first pattern, the second color pair including a second high color and a second low color, the second color pair being visibly different from the first color pair. The processor electronically creates a first layer in an electronic image region by electronically painting the electronic image region using the first electronic pattern ink. The processor electronically creates a second layer in the electronic image region by electronically painting, using the second electronic pattern ink, a second pattern. A print engine renders, using marking materials, the electronic image region on a recording medium such that the when the first pattern is visible, the second pattern is not visible and when the second pattern is visible, the first pattern is not visible.

The first low color may correspond to a single color component marking material. The first high color may be black hi and the first low color may be black low. The second high color may be brown hi and the second low color may be brown low. The first high color may be dark-red hi and the first low color may be dark-red low.

The first structure may be different from the second structure.

A recording medium includes a substrate and marking materials formed on the substrate. The marking materials form, on the substrate, a first layer, the first layer being created using a first color pair and a first pattern, the first color pair including a first high color and a first low color. The marking materials form, on the substrate, a second layer, the second layer being created using a second color pair and a second pattern following the first pattern of the first layer, the second color pair including a second high color and a second low color. The first pattern is visible when viewing the recording medium when the second pattern is not visible when viewing the recording medium. The second pattern is visible when viewing the recording medium when the first pattern is not visible when viewing the recording medium.

The first high color may be black hi and the first low color may be black low. The second high color may be brown hi and the second low color may be brown low. The first high color may be dark-red hi and the first low color may be dark-red low.

The second high color and the second low color may be viewable when using infrared illumination.

The first high color and the first low color may be viewable when using infrared illumination.

The second high color and the second low color may be viewable when using infrared illumination and the first high color and the first low color may be viewable when using infrared illumination.

A method for rendering a gloss effect image pattern on a recording medium (a) electronically creates a first electronic pattern ink, the first electronic pattern ink including a first color and including holes, the holes representing areas in the first electronic pattern ink wherein the first color is absent; (b) electronically creates an electronic image region having a pattern; (c) electronically paints, using the first electronic pattern ink, a background of electronic image region and the pattern of the electronic image region; (d) electronically paints a predetermined portion of the holes within the electronic image region with a second color; and (e) renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle.

The second color may be rendered using a clear marking material.

The second color may be rendered using a single component marking material.

The predetermined portion of the holes painted with the second color may be holes within the pattern of the electronic image region.

The predetermined portion of the holes painted with the second color may be holes within the background of the electronic image region.

A system for rendering a gloss effect image pattern on a recording medium includes a processor for electronically creating a first electronic pattern ink, the first electronic pattern ink including a first color and including holes, the holes representing areas in the first electronic pattern ink wherein the first color is absent. The processor electronically creates an electronic image region having a pattern; electronically painting, using the first electronic pattern ink, a background of the electronic image region and the pattern of the electronic image region; and electronically painting a predetermined portion of the holes within the electronic image region with a second color. A print engine renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle.

The second color may be rendered using a clear marking material.

The second color may be rendered using a single component marking material.

The predetermined portion of the holes painted with the second color may be holes within the pattern of the electronic image region.

The predetermined portion of the holes painted with the second color may be holes within the background of the electronic image region.

A recording medium includes a substrate and marking materials formed on the substrate. The marking materials form, in a first region of the substrate, a first pattern with a non-smooth structure, the non-smooth structure being realized by areas in the first pattern having no marking material formed on the substrate and remaining areas in the first pattern having marking material formed on the substrate. The marking materials form, in a second region of the substrate, a second pattern with a smooth structure, the smooth structure being realized by all areas in the second pattern having a substantially uniform height of marking materials formed on the substrate. The second pattern is visible when a relative angle between an observer's viewing angle and an angle of illuminating the recording medium by an illumination source is a first angle, and the first pattern is not visible when the relative angle between the observer's viewing angle and the angle of illuminating the recording medium by the illumination source is a second angle, the second angle being not equal to the first angle.

The second pattern may include areas having a clear marking material, the clear marking material enabling the substantially uniform height of marking materials formed on the substrate.

The second pattern may include areas having a clear marking material.

The second pattern may include areas having a single component marking material.

A method for rendering a gloss effect image pattern on a recording medium (a) electronically creates a first electronic pattern ink, the first electronic pattern ink including a first color and including holes, the holes representing areas in the first electronic pattern ink wherein the first color is absent; (b) electronically creates a second electronic pattern ink using the first color and including filled holes, the filled holes of the second electronic pattern ink representing areas in the second electronic pattern ink filled with a second color, the second color being different than the first color; (c) electronically creates an electronic image region; (d) electronically paints, using the first electronic pattern ink, a background of the electronic image region; (e) electronically paints, using the second electronic pattern ink, a foreground of the electronic image region; and (e) renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle.

The second color may be rendered using a clear marking material.

The second color may be rendered using a single component marking material.

A system for rendering a gloss effect image pattern on a recording medium includes a processor for electronically creating a first electronic pattern ink, the first electronic pattern ink including a first color and including holes, the holes representing areas in the first electronic pattern ink wherein the first color is absent. The processor electronically creates a second electronic pattern ink using the first color and including filled holes, the filled holes of the second electronic pattern ink representing areas in the second electronic pattern ink filled with a second color, the second color being different than the first color; electronically creates an electronic image region; electronically paints, using the first electronic pattern ink, a background of the electronic image region; and electronically paints, using the second electronic pattern ink, a foreground of the electronic image region. A print engine renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle.

The second color may be rendered using a clear marking material.

The second color may be rendered using a single component marking material.

A method for rendering a gloss effect image pattern on a recording medium (a) electronically creates a first electronic pattern ink, the first electronic pattern ink including a first color and including holes, the holes representing areas in the first electronic pattern ink wherein the first color is absent; (b) electronically creates a second electronic pattern ink using the first color and including filled holes, the filled holes of the second electronic pattern ink representing areas in the second electronic pattern ink filled with a second color, the second color being different than the first color; (c) electronically creates an electronic image region; (d) electronically paints, using the first electronic pattern ink, a foreground of the electronic image region; (e) electronically paints, using the second electronic pattern ink, a background of the electronic image region; and (e) renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle.

The second color may be rendered using a clear marking material.

The second color may be rendered using a single component marking material.

A system for rendering a gloss effect image pattern on a recording medium includes a processor for electronically creating a first electronic pattern ink, the first electronic pattern ink including a first color and including holes, the holes representing areas in the first electronic pattern ink wherein the first color is absent. The processor electronically creates a second electronic pattern ink using the first color and including filled holes, the filled holes of the second electronic pattern ink representing areas in the second electronic pattern ink filled with a second color, the second color being different than the first color; electronically creates an electronic image region; electronically paints, using the first electronic pattern ink, a foreground of the electronic image region; and electronically paints, using the second electronic pattern ink, a background of the electronic image region. A print engine renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle.

The second color may be rendered using a clear marking material.

The second color may be rendered using a single component marking material.

A method for rendering a gloss effect image pattern on a recording medium having a first color (a) electronically creates a first electronic pattern ink, the first electronic pattern ink including a second color and including holes, the holes representing areas in the first electronic pattern ink wherein the second color is absent; (b) electronically creates an electronic image region having a pattern; (c) electronically paints, using the first electronic pattern ink, a background of electronic image region and the pattern of the electronic image region; (d) electronically paints a predetermined portion of the holes within the electronic image region with a third color, the third color matching the first color of the recording medium; and (e) renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

The predetermined portion of the holes painted with the third color may be holes within the pattern of the electronic image region.

The predetermined portion of the holes painted with the third color may be holes within the background of the electronic image region.

A system for rendering a gloss effect image pattern on a recording medium having a first color includes a processor for electronically creating a first electronic pattern ink, the first electronic pattern ink including a second color and including holes, the holes representing areas in the first electronic pattern ink wherein the second color is absent. The processor electronically creates an electronic image region having a pattern; electronically paints, using the first electronic pattern ink, a background of the electronic image region and the pattern of the electronic image region; and electronically paints a predetermined portion of the holes within the electronic image region with a third color, the third color matching the first color of the recording medium. A print engine renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

The predetermined portion of the holes painted with the third color may be holes within the pattern of the electronic image region.

The predetermined portion of the holes painted with the third color may be holes within the background of the electronic image region.

A method for rendering a gloss effect image pattern on a recording medium having a first color (a) electronically creates a first electronic pattern ink, the first electronic pattern ink including a second color and including holes, the holes representing areas in the first electronic pattern ink wherein the second color is absent; (b) electronically creates a second electronic pattern ink using the second color and including filled holes, the filled holes of the second electronic pattern ink representing areas in the second electronic pattern ink filled with a third color, the third color matching the first color of the recording medium; (c) electronically creates an electronic image region; (d) electronically paints, using the first electronic pattern ink, a background of the electronic image region; (e) electronically paints, using the second electronic pattern ink, a foreground of the electronic image region; and (e) renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

A system for rendering a gloss effect image pattern on a recording medium having a first color includes a processor for creating a first electronic pattern ink, the first electronic pattern ink including a second color and including holes, the holes representing areas in the first electronic pattern ink wherein the second color is absent. The processor electronically creates a second electronic pattern ink using the second color and including filled holes, the filled holes of the second electronic pattern ink representing areas in the second electronic pattern ink filled with a third color, the third color matching the first color of the recording medium; electronically creates an electronic image region; electronically paints, using the first electronic pattern ink, a background of the electronic image region; and electronically paints, using the second electronic pattern ink, a foreground of the electronic image region. A print engine renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

A method for rendering a gloss effect image pattern on a recording medium having a first color (a) electronically creates a first electronic pattern ink, the first electronic pattern ink including a second color and including holes, the holes representing areas in the first electronic pattern ink wherein the second color is absent; (b) electronically creates a second electronic pattern ink using the second color and including filled holes, the filled holes of the second electronic pattern ink representing areas in the second electronic pattern ink filled with a third color, the third color matching the first color of the recording medium; (c) electronically creates an electronic image region; (d) electronically paints, using the first electronic pattern ink, a foreground of the electronic image region; (e) electronically paint, using the second electronic pattern ink, a background of the electronic image region; and (e) renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

A system for rendering a gloss effect image pattern on a recording medium having a first color includes a processor for electronically creating a first electronic pattern ink, the first electronic pattern ink including a second color and including holes, the holes representing areas in the first electronic pattern ink wherein the second color is absent. The processor electronically creates a second electronic pattern ink using the second color and including filled holes, the filled holes of the second electronic pattern ink representing areas in the second electronic pattern ink filled with a third color, the third color matching the first color of the recording medium; electronically creates an electronic image region; electronically paints, using the first electronic pattern ink, a foreground of the electronic image region; and electronically paints, using the second electronic pattern ink, a background of the electronic image region. A print engine renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

A method for rendering an ultraviolet image pattern on a recording medium having florescence properties and being a first color, (a) electronically creates a first electronic pattern ink, the first electronic pattern ink including a second color and including holes, the holes representing areas in the first electronic pattern ink wherein the second color is absent; (b) electronically creates an electronic image region having a pattern; (c) electronically paints, using the first electronic pattern ink, a background of the electronic image region and the pattern of the electronic image region; (d) electronically paints a predetermined portion of the holes with a third color, the third color matching the first color of the recording medium; and (e) renders, using marking materials, the electronic image region on the recording medium such that the florescence properties of the recording medium are only visible through the holes not painted with the third color when viewing the recording medium using ultraviolet illumination.

The predetermined portion of the holes painted with the third color may be holes within the pattern of the electronic image region.

The predetermined portion of the holes painted with the third color may be holes within the background of the electronic image region.

A system for rendering an ultraviolet image pattern on a recording medium having florescence properties and being a first color includes a processor for electronically creating a first electronic pattern ink, the first electronic pattern ink including a second color and including holes, the holes representing areas in the first electronic pattern ink wherein the second color is absent. The processor electronically creates an electronic image region having a pattern; electronically paints, using the first electronic pattern ink, a background of the electronic image region and the pattern of the electronic image region; and electronically paints a predetermined portion of the holes with a third color, the third color matching the first color of the recording medium. A print engine renders, using marking materials, the electronic image region on the recording medium such that the florescence properties of the recording medium are only visible through the holes not painted with the third color when viewing the recording medium using ultraviolet illumination.

The predetermined portion of the holes painted with the third color may be holes within the pattern of the electronic image region.

The predetermined portion of the holes painted with the third color may be holes within the background of the electronic image region.

A recording medium includes a substrate having florescence properties and being a first color and marking materials formed on the substrate. The marking materials form, in a first region of the substrate, a first pattern with a non-smooth structure, the non-smooth structure being realized by areas in the first pattern having no marking material formed on the substrate and remaining areas in the first pattern having marking material formed on the substrate. The marking materials form, in a second region of the substrate, a second pattern being realized by all areas in the second pattern having marking materials formed on the substrate. The florescence properties of the substrate may be only visible through the areas in the first pattern having no marking material formed on the substrate when viewing the recording medium using ultraviolet illumination.

A method for rendering an ultraviolet image pattern on a recording medium having florescence properties and a first color (a) electronically creates a first electronic pattern ink, the first electronic pattern ink including a second color, holes, and a first pattern, the holes representing areas in the first electronic pattern ink wherein the second color is absent; (b) electronically creates a second electronic pattern ink, the second electronic pattern ink including the second color, holes, and the first pattern, the holes of the second electronic pattern ink representing areas in the second electronic pattern ink filled with a third color, the third color being equal to the first color; (c) electronically creates an electronic image region having a background and a foreground; (d) electronically paints, using the first electronic pattern ink, the background of the electronic image region; (e) electronically paints, using the second electronic pattern ink, the foreground of the electronic image region; and (f) renders, using marking materials, the electronic image region on a recording medium such that only the florescence properties of the recording medium are only visible through the holes when viewing the recording medium using ultraviolet illumination.

The foreground of the electronic image region may have a second pattern.

The background of the electronic image region may have a second pattern.

A system for rendering an ultraviolet image pattern on a recording medium having florescence properties includes a processor for electronically creating a first electronic pattern ink, the first electronic pattern ink including a second color, holes, and a first pattern, the holes representing areas in the first electronic pattern ink wherein the second color is absent. The processor electronically creates a second electronic pattern ink, the second electronic pattern ink including the second color, holes, and the first pattern, the holes of the second electronic pattern ink representing areas in the second electronic pattern ink filled with a third color, the third color being equal to the first color; electronically creates an electronic image region having a background and a foreground; electronically paints, using the first electronic pattern ink, the background of the electronic image region; and electronically paints, using the second electronic pattern ink, the foreground of the electronic image region. A print engine renders, using marking materials, the electronic image region on a recording medium such that only the florescence properties of the recording medium are only visible through the holes when viewing the recording medium using ultraviolet illumination.

The foreground of the electronic image region may have a second pattern.

The background of the electronic image region may have a second pattern.

A method for rendering an ultraviolet image pattern on a recording medium having florescence properties and a first color (a) electronically creates a first electronic pattern ink, the first electronic pattern ink including a second color, holes, and a first pattern, the holes representing areas in the first electronic pattern ink wherein the second color is absent; (b) electronically creates a second electronic pattern ink, the second electronic pattern ink including the second color, holes, and the first pattern, the holes of the second electronic pattern ink representing areas in the second electronic pattern ink filled with a third color, the third color being equal to the first color; (c) electronically creates an electronic image having a background and a foreground; (d) electronically paints, using the first electronic pattern ink, the background of the image region; (e) electronically paints, using the second electronic pattern ink, the foreground of the image region; and (f) renders, using marking materials, the electronic image region on a recording medium such that only the florescence properties of the recording medium are only visible through the holes when viewing the recording medium using ultraviolet illumination.

The foreground of the electronic image region may have a second pattern.

The background of the electronic image region may have a second pattern.

A system for rendering an ultraviolet image pattern on a recording medium having florescence properties includes a processor for electronically creating a first electronic pattern ink, the first electronic pattern ink including a second color, holes, and a first pattern, the holes representing areas in the first electronic pattern ink wherein the second color is absent. The processor electronically creates a second electronic pattern ink, the second electronic pattern ink including the second color, holes, and the first pattern, the holes of the second electronic pattern ink representing areas in the second electronic pattern ink filled with a third color, the third color being equal to the first color; electronically creates an electronic image region having a background and a foreground; electronically paints, using the first electronic pattern ink, the background of the electronic image region; and electronically paints, using the second electronic pattern ink, the foreground of the electronic image region. A print engine renders, using marking materials, the electronic image region on a recording medium such that only the florescence properties of the recording medium are only visible through the holes when viewing the recording medium using ultraviolet illumination.

The foreground of the electronic image region may have a second pattern.

The background of the electronic image region may have a second pattern.

A method renders an ultraviolet image pattern and a gloss effect pattern on a recording medium having florescence properties and being a first color (a) electronically creates a first electronic pattern ink, the first electronic pattern ink including a second color and including holes, the holes representing areas in the first electronic pattern ink wherein the second color is absent, the second color matching the first color of the recording medium; (b) electronically creates an electronic image region having a pattern; (c) electronically paints, using the first electronic pattern ink, a background of the electronic image region and the pattern of the electronic image region; (d) electronically paints a predetermined portion of the holes with a third color, the third color matching the first color of the recording medium; and (e) renders, using marking materials, the electronic image region on the recording medium such that the florescence properties of the recording medium are only visible through the holes not painted with the third color when viewing the recording medium using ultraviolet illumination and such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

The predetermined portion of the holes painted with the third color may be holes within the pattern of the electronic image region.

The predetermined portion of the holes painted with the third color may be holes within the background of the electronic image region.

A system renders an ultraviolet image pattern and a gloss effect pattern on a recording medium having florescence properties and being a first color includes a processor for electronically creating a first electronic pattern ink, the first electronic pattern ink including a second color and including holes, the holes representing areas in the first electronic pattern ink wherein the second color is absent, the second color matching the first color of the recording medium. The processor electronically creates an electronic image region having a pattern; electronically paints, using the first electronic pattern ink, a background of the electronic image region and the pattern of the electronic image region; and electronically paints a predetermined portion of the holes with a third color, the third color matching the first color of the recording medium. A print engine renders, using marking materials, the electronic image region on the recording medium such that the florescence properties of the recording medium are only visible through the holes not painted with the third color when viewing the recording medium using ultraviolet illumination and such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

The predetermined portion of the holes painted with the third color may be holes within the pattern of the electronic image region.

The predetermined portion of the holes painted with the third color may be holes within the background of the electronic image region.

A method renders an ultraviolet image pattern and a gloss effect pattern on a recording medium having florescence properties and being a first color (a) electronically creates a first electronic pattern ink, the first electronic pattern ink including a second color, holes, and a first pattern, the holes representing areas in the first electronic pattern ink wherein the second color is absent; (b) electronically creates a second electronic pattern ink, the second electronic pattern ink including the second color, holes, and the first pattern, the holes of the second electronic pattern ink representing areas in the second electronic pattern ink filled with a third color, the third color being equal to the first color; (c) electronically creates an electronic image region having a background and a foreground; (d) electronically paints, using the first electronic pattern ink, the background of the electronic image region; (e) electronically paints, using the second electronic pattern ink, the foreground of the electronic image region; and (f) renders, using marking materials, the electronic image region on a recording medium such that only the florescence properties of the recording medium are only visible through the holes when viewing the recording medium using ultraviolet illumination and such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

The foreground of the electronic image region may have a second pattern.

The background of the electronic image region may have a second pattern.

A system renders an ultraviolet image pattern and a gloss effect pattern on a recording medium having florescence properties and being a first color includes a processor for electronically creating a first electronic pattern ink, the first electronic pattern ink including a second color, holes, and a first pattern, the holes representing areas in the first electronic pattern ink wherein the second color is absent. The processor electronically creates a second electronic pattern ink, the second electronic pattern ink including the second color, holes, and the first pattern, the holes of the second electronic pattern ink representing areas in the second electronic pattern ink filled with a third color, the third color being equal to the first color; electronically creates an electronic image region having a background and a foreground; electronically paints, using the first electronic pattern ink, the background of the electronic image region; and electronically paints, using the second electronic pattern ink, the foreground of the electronic image region. A print engine renders, using marking materials, the electronic image region on a recording medium such that only the florescence properties of the recording medium are only visible through the holes when viewing the recording medium using ultraviolet illumination and such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

The foreground of the electronic image region may have a second pattern.

The background of the electronic image region may have a second pattern.

A method renders an ultraviolet image pattern and a gloss effect pattern on a recording medium having florescence properties and being a first color (a) electronically creates a first electronic pattern ink, the first electronic pattern ink including a second color, holes, and a first pattern, the holes representing areas in the first electronic pattern ink wherein the second color is absent; (b) electronically creates a second electronic pattern ink, the second electronic pattern ink including the second color, holes, and the first pattern, the holes of the second electronic pattern ink representing areas in the second electronic pattern ink filled with a third color, the third color being equal to the first color; (c) electronically creates an electronic image having a background and a foreground; (d) electronically paints, using the first electronic pattern ink, the background of the image region; (e) electronically paints, using the second electronic pattern ink, the foreground of the image region; and (f) renders, using marking materials, the electronic image region on a recording medium such that only the florescence properties of the recording medium are only visible through the holes when viewing the recording medium using ultraviolet illumination and such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

The foreground of the electronic image region may have a second pattern.

The background of the electronic image region may have a second pattern.

A system renders an ultraviolet image pattern and a gloss effect pattern on a recording medium having florescence properties and being a first color includes a processor for electronically creating a first electronic pattern ink, the first electronic pattern ink including a second color, holes, and a first pattern, the holes representing areas in the first electronic pattern ink wherein the second color is absent. The processor electronically creates a second electronic pattern ink, the second electronic pattern ink including the second color, holes, and the first pattern, the holes of the second electronic pattern ink representing areas in the second electronic pattern ink filled with a third color, the third color being equal to the first color; electronically creates an electronic image region having a background and a foreground; electronically paints, using the first electronic pattern ink, the background of the electronic image region; and electronically paints, using the second electronic pattern ink, the foreground of the electronic image region. A print engine renders, using marking materials, the electronic image region on a recording medium such that only the florescence properties of the recording medium are only visible through the holes when viewing the recording medium using ultraviolet illumination and such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

The foreground of the electronic image region may have a second pattern.

The background of the electronic image region may have a second pattern.

A method renders an infrared image pattern and a gloss effect image pattern on a recording medium (a) electronically creates a first electronic pattern ink, the first electronic pattern ink including a first color and including holes, the holes representing areas in the first electronic pattern ink wherein the first color is absent; (b) electronically creates an electronic image region having a pattern; (c) electronically paints, using the first electronic pattern ink, a background of electronic image region and the pattern of the electronic image region; (d) electronically paints a predetermined portion of the holes within the electronic image region with a second color, the second color having infrared properties opposite of infrared properties of the recording medium; and (e) renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle and such that the recording medium is only visible through the holes not painted with the second color when viewing the recording medium using infrared illumination.

The predetermined portion of the holes painted with the second color may be holes within the pattern of the electronic image region.

The predetermined portion of the holes painted with the second color may be holes within the background of the electronic image region.

A system renders an infrared image pattern and a gloss effect image pattern on a recording medium includes a processor for electronically creating a first electronic pattern ink, the first electronic pattern ink including a first color and including holes, the holes representing areas in the first electronic pattern ink wherein the first color is absent. The processor electronically creates an electronic image region having a pattern; electronically paints, using the first electronic pattern ink, a background of the electronic image region and the pattern of the electronic image region; and electronically paints a predetermined portion of the holes within the electronic image region with a second color, the second color having infrared properties opposite of infrared properties of the recording medium. A print engine renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle and such that the recording medium is only visible through the holes not painted with the second color when viewing the recording medium using infrared illumination.

The predetermined portion of the holes painted with the second color may be holes within the pattern of the electronic image region.

The predetermined portion of the holes painted with the second color may be holes within the background of the electronic image region.

A method renders an infrared image pattern and a gloss effect image pattern on a recording medium (a) electronically creates a first electronic pattern ink, the first electronic pattern ink including a first color and including holes, the holes representing areas in the first electronic pattern ink wherein the first color is absent; (b) electronically creates a second electronic pattern ink using the first color and including filled holes, the filled holes of the second electronic pattern ink representing areas in the second electronic pattern ink filled with a second color, the second color having infrared properties opposite of infrared properties of the recording medium; (c) electronically creates an electronic image region; (d) electronically paints, using the first electronic pattern ink, a background of the electronic image region; (e) electronically paints, using the second electronic pattern ink, a foreground of the electronic image region; and (f) renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle and such that the recording medium is only visible through the holes not painted with the second color when viewing the recording medium using infrared illumination.

The foreground of the electronic image region may have a second pattern.

The background of the electronic image region may have a second pattern.

A system renders an infrared image pattern and a gloss effect image pattern on a recording medium includes a processor for electronically creating a first electronic pattern ink, the first electronic pattern ink including a first color and including holes, the holes representing areas in the first electronic pattern ink wherein the first color is absent. The processor electronically creates a second electronic pattern ink using the first color and including filled holes, the filled holes of the second electronic pattern ink representing areas in the second electronic pattern ink filled with a second color, the second color having infrared properties opposite of infrared properties of the recording medium; electronically creates an electronic image region; electronically paints, using the first electronic pattern ink, a background of the electronic image region; and electronically paints, using the second electronic pattern ink, a foreground of the electronic image region. A print engine renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle and such that the recording medium is only visible through the holes not painted with the second color when viewing the recording medium using infrared illumination.

The foreground of the electronic image region may have a second pattern.

The background of the electronic image region may have a second pattern.

A method renders an infrared image pattern and a gloss effect image pattern on a recording medium (a) electronically creates a first electronic pattern ink, the first electronic pattern ink including a first color and including holes, the holes representing areas in the first electronic pattern ink wherein the first color is absent; (b) electronically creates a second electronic pattern ink using the first color and including filled holes, the filled holes of the second electronic pattern ink representing areas in the second electronic pattern ink filled with a second color, the second color having infrared properties opposite of infrared properties of the recording medium; (c) electronically creates an electronic image region; (d) electronically paints, using the first electronic pattern ink, a foreground of the electronic image region; (e) electronically paints, using the second electronic pattern ink, a background of the electronic image region; and (f) renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle and such that the recording medium is only visible through the holes not painted with the second color when viewing the recording medium using infrared illumination.

The foreground of the electronic image region may have a second pattern.

The background of the electronic image region may have a second pattern.

A system renders an infrared image pattern and a gloss effect image pattern on a recording medium includes a processor for electronically creating a first electronic pattern ink, the first electronic pattern ink including a first color and including holes, the holes representing areas in the first electronic pattern ink wherein the first color is absent. The processor electronically creates a second electronic pattern ink using the first color and including filled holes, the filled holes of the second electronic pattern ink representing areas in the second electronic pattern ink filled with a second color, the second color having infrared properties opposite of infrared properties of the recording medium; electronically creates an electronic image region; electronically paints, using the first electronic pattern ink, a foreground of the electronic image region; and electronically paints, using the second electronic pattern ink, a background of the electronic image region. A print engine renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle and such that the recording medium is only visible through the holes not painted with the second color when viewing the recording medium using infrared illumination.

The foreground of the electronic image region may have a second pattern.

The background of the electronic image region may have a second pattern.

A method renders an infrared image pattern on a recording medium having a first color (a) electronically creates a first electronic pattern ink, the first electronic pattern ink including a second color and including holes, the holes representing areas in the first electronic pattern ink wherein the second color is absent; (b) electronically creates an electronic image region having a pattern; (c) electronically paints, using the first electronic pattern ink, a background of electronic image region and the pattern of the electronic image region; (d) electronically paints a predetermined portion of the holes within the electronic image region with a third color, the third color being equal to the first color but having opposite infrared properties; and (e) renders, using marking materials, the electronic image region on the recording medium such that the recording medium is only visible through the holes not painted with the third color when viewing the recording medium using infrared illumination and such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle.

The predetermined portion of the holes painted with the third color may be holes within the pattern of the electronic image region.

The predetermined portion of the holes painted with the third color may be holes within the background of the electronic image region.

The recording medium may be a black media in which an infrared camera detects light and the third color is black.

The recording medium may be a dark red media in which an infrared camera detects light and the third color is dark red.

A system renders an infrared image pattern on a recording medium having a first color includes a processor for electronically creating a first electronic pattern ink, the first electronic pattern ink including a second color and including holes, the holes representing areas in the first electronic pattern ink wherein the second color is absent. The processor electronically creates an electronic image region having a pattern; electronically paints a predetermined portion of the holes within the electronic image region with a third color, the third color being equal to the first color but having opposite infrared properties; and electronically paints a predetermined portion of the holes within the electronic image region with a third color, the third color being equal to the first color but having opposite infrared properties. A print engine renders, using marking materials, the electronic image region on the recording medium such that the recording medium is only visible through the holes not painted with the third color when viewing the recording medium using infrared illumination and such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle.

The predetermined portion of the holes painted with the third color may be holes within the pattern of the electronic image region.

The predetermined portion of the holes painted with the third color may be holes within the background of the electronic image region.

The recording medium may be a black media in which an infrared camera detects light and the third color is black.

The recording medium may be a dark red media in which an infrared camera detects light and the third color is dark red.

A method renders an infrared image pattern on a recording medium having a first color (a) electronically creates a first electronic pattern ink, the first electronic pattern ink including a second color and including holes, the holes representing areas in the first electronic pattern ink wherein the second color is absent; (b) electronically creates a second electronic pattern ink using the second color and including filled holes, the filled holes of the second electronic pattern ink representing areas in the second electronic pattern ink filled with a second color, the second color having infrared properties opposite of infrared properties of the recording medium; (c) electronically creates an electronic image region; (d) electronically paints, using the first electronic pattern ink, a background of the electronic image region; (e) electronically paints, using the second electronic pattern ink, a foreground of the electronic image region; and (f) renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle and such that the recording medium is only visible through the holes not painted with the second color when viewing the recording medium using infrared illumination.

The foreground of the electronic image region may have a second pattern.

The background of the electronic image region may have a second pattern.

A system renders an infrared image pattern on a recording medium having a first color includes a processor for electronically creating a first electronic pattern ink, the first electronic pattern ink including a second color and including holes, the holes representing areas in the first electronic pattern ink wherein the second color is absent. The processor electronically creates a second electronic pattern ink using the first color and including filled holes, the filled holes of the second electronic pattern ink representing areas in the second electronic pattern ink filled with a second color, the second color having infrared properties opposite of infrared properties of the recording medium; electronically creates an electronic image region; electronically paints, using the first electronic pattern ink, a background of the electronic image region; and electronically paints, using the second electronic pattern ink, a foreground of the electronic image region. A print engine renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle and such that the recording medium is only visible through the holes not painted with the second color when viewing the recording medium using infrared illumination.

The foreground of the electronic image region may have a second pattern.

The background of the electronic image region may have a second pattern.

A method renders an infrared image pattern on a recording medium having a first color (a) electronically creates a first electronic pattern ink, the first electronic pattern ink including a second color and including holes, the holes representing areas in the first electronic pattern ink wherein the second color is absent; (b) electronically creates a second electronic pattern ink using the first color and including filled holes, the filled holes of the second electronic pattern ink representing areas in the second electronic pattern ink filled with a second color, the second color having infrared properties opposite of infrared properties of the recording medium; (c) electronically creates an electronic image region; (d) electronically paints, using the first electronic pattern ink, a foreground of the electronic image region; (e) electronically paints, using the second electronic pattern ink, a background of the electronic image region; and (f) renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle and such that the recording medium is only visible through the holes not painted with the second color when viewing the recording medium using infrared illumination and such that the recording medium is only visible through the holes not painted with the second color when viewing the recording medium using infrared illumination.

The foreground of the electronic image region may have a second pattern.

The background of the electronic image region may have a second pattern.

A system renders an infrared image pattern on a recording medium having a first color includes a processor for electronically creating a first electronic pattern ink, the first electronic pattern ink including a second color and including holes, the holes representing areas in the first electronic pattern ink wherein the second color is absent. The processor electronically creates a second electronic pattern ink using the first color and including filled holes, the filled holes of the second electronic pattern ink representing areas in the second electronic pattern ink filled with a second color, the second color having infrared properties opposite of infrared properties of the recording medium; electronically creates an electronic image region; electronically paints, using the first electronic pattern ink, a foreground of the electronic image region; and electronically paints, using the second electronic pattern ink, a background of the electronic image region. A print engine renders, using marking materials, the electronic image region on the recording medium such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle and such that the recording medium is only visible through the holes not painted with the second color when viewing the recording medium using infrared illumination and such that the recording medium is only visible through the holes not painted with the second color when viewing the recording medium using infrared illumination.

The foreground of the electronic image region may have a second pattern.

The background of the electronic image region may have a second pattern.

A method renders an ultraviolet image pattern and a gloss effect pattern on a recording medium having florescence properties (a) electronically creates a first electronic pattern ink, the first electronic pattern ink including a first color and including holes, the holes representing areas in the first electronic pattern ink wherein the first color is absent; (b) electronically creates an electronic image region having a pattern; (c) electronically paints, using the first electronic pattern ink, a background of the electronic image region and the pattern of the electronic image region; (d) electronically paints a predetermined portion of the holes with a second color; and (e) renders, using marking materials, the electronic image region on the recording medium such that the florescence properties of the recording medium are only visible through the holes not painted with the second color when viewing the recording medium using ultraviolet illumination and such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle.

The predetermined portion of the holes painted with the second color may be holes within the pattern of the electronic image region.

The predetermined portion of the holes painted with the second color may be holes within the background of the electronic image region.

A system renders an ultraviolet image pattern and a gloss effect pattern on a recording medium having florescence properties includes a processor for electronically creating a first electronic pattern ink, the first electronic pattern ink including a first color and including holes, the holes representing areas in the first electronic pattern ink wherein the first color is absent. The processor electronically creates an electronic image region having a pattern; electronically paints, using the first electronic pattern ink, a background of the electronic image region and the pattern of the electronic image region; and electronically paints a predetermined portion of the holes with a second color. A print engine renders, using marking materials, the electronic image region on the recording medium such that the florescence properties of the recording medium are only visible through the holes not painted with the second color when viewing the recording medium using ultraviolet illumination and such that the electronic image region is visible when a relative angle between an observer's viewing angle and an angle of illuminating the recording medium by an illumination source is a first angle, the electronic image region not having the predetermined portion of the holes painted with the second color being not visible when the relative angle between the observer's viewing angle and the angle of illuminating the recording medium by the illumination source is a second angle, the second angle being not equal to the first angle.

The predetermined portion of the holes painted with the second color may be holes within the pattern of the electronic image region.

The predetermined portion of the holes painted with the second color may be holes within the background of the electronic image region.

A method renders an ultraviolet image pattern and a gloss effect pattern on a recording medium having florescence properties (a) electronically creates a first electronic pattern ink, the first electronic pattern ink including a first color, holes, and a first pattern, the holes representing areas in the first electronic pattern ink wherein the first color is absent; (b) electronically creates a second electronic pattern ink, the second electronic pattern ink including the first color, holes, and the first pattern, the holes of the second electronic pattern ink representing areas in the second electronic pattern ink filled with a second color; (c) electronically creates an electronic image region having a background and a foreground; (d) electronically paints, using the first electronic pattern ink, the background of the electronic image region; (e) electronically paints, using the second electronic pattern ink, the foreground of the electronic image region; and (f) renders, using marking materials, the electronic image region on a recording medium such that only the florescence properties of the recording medium are only visible through the holes when viewing the recording medium using ultraviolet illumination and such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

The foreground of the electronic image region may have a second pattern.

The background of the electronic image region may have a second pattern.

A system renders an ultraviolet image pattern and a gloss effect pattern on a recording medium having florescence properties includes a processor for electronically creating a first electronic pattern ink, the first electronic pattern ink including a first color, holes, and a first pattern, the holes representing areas in the first electronic pattern ink wherein the first color is absent. The processor electronically creates a second electronic pattern ink, the second electronic pattern ink including the first color, holes, and the first pattern, the holes of the second electronic pattern ink representing areas in the second electronic pattern ink filled with a second color; electronically creates an electronic image region having a background and a foreground; electronically paints, using the first electronic pattern ink, the background of the electronic image region; and electronically paints, using the second electronic pattern ink, the foreground of the electronic image region. A print engine renders, using marking materials, the electronic image region on a recording medium such that only the florescence properties of the recording medium are only visible through the holes when viewing the recording medium using ultraviolet illumination and such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

The foreground of the electronic image region may have a second pattern.

The background of the electronic image region may have a second pattern.

A method renders an ultraviolet image pattern and a gloss effect pattern on a recording medium having florescence properties (a) electronically creates a first electronic pattern ink, the first electronic pattern ink including a first color, holes, and a first pattern, the holes representing areas in the first electronic pattern ink wherein the first color is absent; (b) electronically creates a second electronic pattern ink, the second electronic pattern ink including the first color, holes, and the first pattern, the holes of the second electronic pattern ink representing areas in the second electronic pattern ink filled with a second color; (c) electronically creates an electronic image having a background and a foreground; (d) electronically paints, using the first electronic pattern ink, the background of the image region; (e) electronically paints, using the second electronic pattern ink, the foreground of the image region; and (f) renders, using marking materials, the electronic image region on a recording medium such that only the florescence properties of the recording medium are only visible through the holes when viewing the recording medium using ultraviolet illumination and such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

The foreground of the electronic image region may have a second pattern.

The background of the electronic image region may have a second pattern.

A system renders an ultraviolet image pattern and a gloss effect pattern on a recording medium having florescence properties includes a processor for electronically creating a first electronic pattern ink, the first electronic pattern ink including a first color, holes, and a first pattern, the holes representing areas in the first electronic pattern ink wherein the first color is absent. The processor electronically creates a second electronic pattern ink, the second electronic pattern ink including the second color, holes, and the first pattern, the holes of the second electronic pattern ink representing areas in the second electronic pattern ink filled with a second color; electronically creates an electronic image region having a background and a foreground; electronically paints, using the first electronic pattern ink, the background of the electronic image region; and electronically paints, using the second electronic pattern ink, the foreground of the electronic image region. A print engine renders, using marking materials, the electronic image region on a recording medium such that only the florescence properties of the recording medium are only visible through the holes when viewing the recording medium using ultraviolet illumination and such that the electronic image region is visible when a relative angle between an observer's viewing angle and an angle of illuminating the recording medium by an illumination source is a first angle, the electronic image region not having the predetermined portion of the holes painted with the third color being not visible when the relative angle between the observer's viewing angle and the angle of illuminating the recording medium by the illumination source is a second angle, the second angle being not equal to the first angle.

The foreground of the electronic image region may have a second pattern.

The background of the electronic image region may have a second pattern.

It will be appreciated that several of the above-disclosed embodiments and other features and functions, or alternatives thereof, may be desirably combined into many other different systems or applications. Also, various presently unforeseen or unanticipated alternatives, modifications, variations, or improvements therein may be subsequently made by those skilled in the art which are also intended to be encompassed by the description above and the following claims.

What is claimed is:

1. A method for rendering a gloss effect image pattern on a recording medium, comprising:
    (a) electronically creating a first electronic pattern ink, said first electronic pattern ink including a first color and including holes, said holes representing areas in said first electronic pattern ink wherein said first color is absent;
    (b) electronically creating a second electronic pattern ink using said first color and including filled holes, said filled holes of said second electronic pattern ink representing areas in the second electronic pattern ink filled with a second color, said second color being different than the first color;
    (c) electronically creating an electronic image region;
    (d) electronically painting, using said first electronic pattern ink, a background of said electronic image region;
    (e) electronically painting, using said second electronic pattern ink, a foreground of said electronic image region; and
    (f) rendering, using marking materials, said electronic image region on the recording medium such that said electronic image region is visible when a relative angle between an observer's viewing angle and an angle of illuminating the recording medium by an illumination source is a first angle, said electronic image region not having said predetermined portion of said holes painted with said second color being not visible when the relative angle between the observer's viewing angle and the angle of illuminating the recording medium by the illumination source is a second angle, said electronic image region having said predetermined portion of said holes painted with said second color being visible when the relative angle between the observer's viewing angle and the angle of illuminating the recording medium by the illumination source is said second angle, said second angle being not equal to said first angle.

2. The method as claimed in claim 1, wherein said second color is rendered using a clear marking material.

3. The method as claimed in claim 1, wherein said second color is rendered using a single component marking material.

4. A system for rendering a gloss effect image pattern on a recording medium, comprising:
    a processor for electronically creating a first electronic pattern ink, said first electronic pattern ink including a first color and including holes, said holes representing areas in said first electronic pattern ink wherein said first color is absent; and
    said processor electronically creating a second electronic pattern ink using said first color and including filled holes, said filled holes of said second electronic pattern ink representing areas in the second electronic pattern ink filled with a second color, said second color being different than the first color;

said processor electronically creating an electronic image region;

said processor electronically painting, using said first electronic pattern ink, a background of said electronic image region;

said processor electronically painting, using said second electronic pattern ink, a foreground of said electronic image region;

a print engine for rendering, using marking materials, said electronic image region on the recording medium such that said electronic image region is visible when a relative angle between an observer's viewing angle and an angle of illuminating the recording medium by an illumination source is a first angle, said electronic image region not having said predetermined portion of said holes painted with said second color being not visible when the relative angle between the observer's viewing angle and the angle of illuminating the recording medium by the illumination source is a second angle, said electronic image region having said predetermined portion of said holes painted with said second color being visible when the relative angle between the observer's viewing angle and the angle of illuminating the recording medium by the illumination source is said second angle, said second angle being not equal to said first angle.

5. The system as claimed in claim 4, wherein said second color is rendered using a clear marking material.

6. The system as claimed in claim 4, wherein said second color is rendered using a single component marking material.

7. A method for rendering a gloss effect image pattern on a recording medium, comprising:

(a) electronically creating a first electronic pattern ink, said first electronic pattern ink including a first color and including holes, said holes representing areas in said first electronic pattern ink wherein said first color is absent;

(b) electronically creating a second electronic pattern ink using said first color and including filled holes, said filled holes of said second electronic pattern ink representing areas in the second electronic pattern ink filled with a second color, said second color being different than the first color;

(c) electronically creating an electronic image region;

(d) electronically painting, using said first electronic pattern ink, a foreground of said electronic image region;

(e) electronically painting, using said second electronic pattern ink, a background of said electronic image region; and (f) rendering, using marking materials, said electronic image region on the recording medium such that said electronic image region is visible when a relative angle between an observer's viewing angle and an angle of illuminating the recording medium by an illumination source is a first angle, said electronic image region not having said predetermined portion of said holes painted with said second color being not visible when the relative angle between the observer's viewing angle and the angle of illuminating the recording medium by the illumination source is a second angle, said electronic image region having said predetermined portion of said holes painted with said second color being visible when the relative angle between the observer's viewing angle and the angle of illuminating the recording medium by the illumination source is said second angle, said second angle being not equal to said first angle.

8. The method as claimed in claim 7, wherein said second color is rendered using a clear marking material.

9. The method as claimed in claim 7, wherein said second color is rendered using a single component marking material.

10. A system for rendering a gloss effect image pattern on a recording medium, comprising:

a processor for electronically creating a first electronic pattern ink, said first electronic pattern ink including a first color and including holes, said holes representing areas in said first electronic pattern ink wherein said first color is absent; and said processor electronically creating a second electronic pattern ink using said first color and including filled holes, said filled holes of said second electronic pattern ink representing areas in the second electronic pattern ink filled with a second color, said second color being different than the first color;

said processor electronically creating an electronic image region;

said processor electronically painting, using said first electronic pattern ink, a foreground of said electronic image region;

said processor electronically painting, using said second electronic pattern ink, a background of said electronic image region;

a print engine for rendering, using marking materials, said electronic image region on the recording medium such that said electronic image region is visible when a relative angle between an observer's viewing angle and an angle of illuminating the recording medium by an illumination source is a first angle, said electronic image region not having said predetermined portion of said holes painted with said second color being not visible when the relative angle between the observer's viewing angle and the angle of illuminating the recording medium by the illumination source is a second angle, said electronic image region having said predetermined portion of said holes painted with said second color being visible when the relative angle between the observer's viewing angle and the angle of illuminating the recording medium by the illumination source is said second angle, said second angle being not equal to said first angle.

11. The system as claimed in claim 10, wherein said second color is rendered using a clear marking material.

12. The system as claimed in claim 10, wherein said second color is rendered using a single component marking material.

* * * * *